(12) United States Patent
Hashimshony et al.

(10) Patent No.: US 7,809,425 B2
(45) Date of Patent: Oct. 5, 2010

(54) METHOD AND APPARATUS FOR EXAMINING A SUBSTANCE, PARTICULARLY TISSUE, TO CHARACTERIZE ITS TYPE

(75) Inventors: Dan Hashimshony, Givat Ada (IL); Gil Cohen, Jerusalem (IL)

(73) Assignee: Dune Medical Devices Ltd., Caesaria (IL)

( * ) Notice: Subject to any disclaimer, the term of this patent is extended or adjusted under 35 U.S.C. 154(b) by 994 days.

(21) Appl. No.: 11/487,431

(22) Filed: Jul. 17, 2006

(65) Prior Publication Data

US 2006/0264738 A1 Nov. 23, 2006

Related U.S. Application Data

(63) Continuation-in-part of application No. 10/891,750, filed on Jul. 15, 2004, now Pat. No. 7,082,325.

(60) Provisional application No. 60/481,130, filed on Jul. 24, 2003.

(51) Int. Cl.
*A61B 5/055* (2006.01)
(52) U.S. Cl. .................. 600/411; 600/420; 600/421; 600/547
(58) Field of Classification Search ........... 600/411, 600/421, 422, 547, 420, 431; 324/309
See application file for complete search history.

(56) References Cited

U.S. PATENT DOCUMENTS

| 3,830,224 A | 8/1974 | Vanzetti et al. |
| RE30,317 E | 7/1980 | Lübbers et al. |
| 4,291,708 A | 9/1981 | Frei et al. |

(Continued)

FOREIGN PATENT DOCUMENTS

DE 3637549 5/1988

(Continued)

OTHER PUBLICATIONS

Partial International Search Dated Sep. 1, 2008 From the International Searching Authority Re.: Application No. PCT/IL2008/000406.

(Continued)

*Primary Examiner*—Ruth S Smith
*Assistant Examiner*—Christopher Cook

(57) ABSTRACT

A method and apparatus are disclosed, for examining a substance of a given volume to characterize its type, with an integrated sensing head. The method comprises applying locally to the substance of the given volume a polarizing magnetic field, with a component defining a polarizing axis; applying locally RF pulses to the substance of the given volume, the RF pulses having a B component, orthogonal to the polarizing axis, such as to invoke EI response signals corresponding to the electrical impedance (EI) of the examined substance of the given volume, and magnetic resonance (MR) response signals corresponding to the MR properties of the examined substance of the given volume; detecting locally EI response signals from the substance of the given volume; and detecting locally MR response signals from the substance of the given volume. Two or more sensing heads may be used, both applying locally the RF pulses and detecting. Alternatively, one of the sensing heads may operate as a transmitter, while the other or others may operate as receivers.

64 Claims, 21 Drawing Sheets

U.S. PATENT DOCUMENTS

| | | | |
|---|---|---|---|
| 4,344,440 | A | 8/1982 | Aaby et al. |
| 4,458,694 | A | 7/1984 | Sollish et al. |
| 4,537,203 | A | 8/1985 | Machida |
| 4,539,640 | A | 9/1985 | Fry et al. |
| RE32,000 | E | 10/1985 | Sagi |
| 4,617,939 | A | 10/1986 | Brown et al. |
| 4,625,171 | A | 11/1986 | Sekihara et al. |
| 4,682,594 | A | 7/1987 | Mok |
| 4,689,567 | A | 8/1987 | Maudsley |
| 4,751,464 | A | 6/1988 | Bridges |
| 4,768,513 | A | 9/1988 | Suzuki |
| 4,779,624 | A | 10/1988 | Yokoi |
| 4,785,806 | A | 11/1988 | Deckelbaum |
| 5,115,137 | A | 5/1992 | Andersson-Engels et al. |
| 5,143,079 | A | 9/1992 | Frei et al. |
| 5,227,730 | A | 7/1993 | King et al. |
| 5,277,730 | A | 1/1994 | Darsey et al. |
| 5,334,941 | A | 8/1994 | King |
| 5,383,454 | A | 1/1995 | Bucholz |
| 5,442,290 | A | 8/1995 | Crooks |
| 5,482,041 | A | 1/1996 | Wilk et al. |
| 5,482,047 | A | 1/1996 | Nordgren et al. |
| 5,558,092 | A | 9/1996 | Unger et al. |
| 5,572,132 | A | 11/1996 | Pulyer et al. |
| 5,630,426 | A | 5/1997 | Eggers et al. |
| 5,678,565 | A | 10/1997 | Sarvazyan |
| 5,699,804 | A | 12/1997 | Rattner |
| 5,704,355 | A | 1/1998 | Bridges |
| 5,727,569 | A | 3/1998 | Benetti et al. |
| 5,735,278 | A | 4/1998 | Hoult et al. |
| 5,744,971 | A | 4/1998 | Chan et al. |
| 5,758,646 | A | 6/1998 | Van Der Meulen et al. |
| 5,800,350 | A | 9/1998 | Coppelson et al. |
| 5,807,257 | A | 9/1998 | Bridges |
| 5,810,742 | A | 9/1998 | Pearlman |
| 5,821,410 | A | 10/1998 | Xiang et al. |
| 5,829,437 | A | 11/1998 | Bridges et al. |
| 5,884,239 | A | 3/1999 | Romanik, Jr. |
| 5,900,618 | A | 5/1999 | Anlage et al. |
| 5,927,284 | A | 7/1999 | Borst et al. |
| 6,004,263 | A | 12/1999 | Nakaichi et al. |
| 6,010,455 | A | 1/2000 | Barnett et al. |
| 6,026,323 | A | 2/2000 | Skladnev et al. |
| 6,055,451 | A | 4/2000 | Bambot et al. |
| 6,055,452 | A | 4/2000 | Pearlman |
| 6,061,589 | A | 5/2000 | Bridges et al. |
| 6,064,081 | A | 5/2000 | Robinson et al. |
| 6,071,239 | A | 6/2000 | Cribbs et al. |
| 6,081,738 | A | 6/2000 | Hinohara et al. |
| 6,086,534 | A | 7/2000 | Kesten |
| 6,090,041 | A | 7/2000 | Clark et al. |
| 6,093,150 | A | 7/2000 | Chandler et al. |
| 6,109,270 | A | 8/2000 | Mah et al. |
| 6,135,968 | A | 10/2000 | Brounstein |
| 6,167,297 | A | 12/2000 | Benaron |
| 6,173,604 | B1 | 1/2001 | Xiang et al. |
| 6,315,981 | B1 | 1/2001 | Unger |
| 6,203,533 | B1 | 3/2001 | Ouchi |
| 6,233,479 | B1 | 5/2001 | Haddad et al. |
| 6,258,576 | B1 | 7/2001 | Richards-Kortum et al. |
| 6,280,704 | B1 | 8/2001 | Schutt et al. |
| 6,287,302 | B1 | 9/2001 | Berube |
| 6,308,097 | B1 | 10/2001 | Pearlman |
| 6,321,106 | B1 | 11/2001 | Lemelson |
| 6,331,166 | B1 | 12/2001 | Burbank et al. |
| 6,375,634 | B1 | 4/2002 | Carroll |
| 6,377,841 | B1 | 4/2002 | Lin et al. |
| 6,380,747 | B1 | 4/2002 | Goldfine et al. |
| 6,397,095 | B1 | 5/2002 | Eyuboglu et al. |
| 6,405,733 | B1 | 6/2002 | Fogarty et al. |
| 6,411,103 | B1 | 6/2002 | Tobias et al. |
| 6,370,426 | B1 | 9/2002 | Campbell et al. |
| 6,500,112 | B1 | 12/2002 | Khouri |
| 6,530,944 | B2 | 3/2003 | West et al. |
| 6,544,185 | B2 | 4/2003 | Montegrande |
| 6,546,787 | B1 | 4/2003 | Schiller et al. |
| 6,564,806 | B1 | 5/2003 | Fogarty et al. |
| 6,592,520 | B1 | 7/2003 | Peszynski et al. |
| 6,597,185 | B1 | 7/2003 | Talanov et al. |
| 6,671,540 | B1 | 12/2003 | Hochman |
| 6,677,755 | B2 | 1/2004 | Belt et al. |
| 6,695,782 | B2 | 2/2004 | Ranucci et al. |
| 6,813,515 | B2 | 2/2004 | Hashimshony |
| 6,699,206 | B2 | 3/2004 | Burbank et al. |
| 6,722,371 | B1 | 4/2004 | Fogarty et al. |
| 6,728,565 | B2 | 4/2004 | Wendlandt |
| 6,741,077 | B2 | 5/2004 | Yokoyama et al. |
| 6,752,154 | B2 | 6/2004 | Fogarty et al. |
| 6,766,185 | B2 | 7/2004 | Scott |
| 6,747,454 | B2 | 8/2004 | Belt |
| 6,840,948 | B2 | 1/2005 | Albrecht et al. |
| 6,909,084 | B2 | 6/2005 | Tachi et al. |
| 6,936,003 | B2 | 8/2005 | Iddan |
| 6,962,587 | B2 | 11/2005 | Johnson et al. |
| 7,082,325 | B2 | 7/2006 | Hashimshony et al. |
| 7,184,824 | B2 | 2/2007 | Hashimshony |
| 2001/0051774 | A1 | 12/2001 | Littrup et al. |
| 2002/0055754 | A1 | 5/2002 | Ranucci et al. |
| 2002/0059938 | A1 | 5/2002 | Fogarty et al. |
| 2002/0068880 | A1 | 6/2002 | Burbank et al. |
| 2002/0120265 | A1 | 8/2002 | Fowler |
| 2002/0148277 | A1 | 10/2002 | Umeda |
| 2003/0036674 | A1 | 2/2003 | Bouton |
| 2003/0187366 | A1 | 2/2003 | Hashimshony |
| 2003/0062897 | A1 | 4/2003 | Belt et al. |
| 2003/0045798 | A1 | 6/2003 | Hular et al. |
| 2003/0117140 | A1 | 6/2003 | Belt et al. |
| 2003/0138378 | A1 | 7/2003 | Hashimshony |
| 2003/0146814 | A1 | 8/2003 | Wiltshire |
| 2003/0163037 | A1 | 8/2003 | Bladen et al. |
| 2003/0171664 | A1 | 9/2003 | Wendlandt |
| 2003/0187347 | A1 | 10/2003 | Nevo et al. |
| 2003/0199753 | A1 | 10/2003 | Hibner et al. |
| 2003/0216648 | A1 | 11/2003 | Lizzi et al. |
| 2003/0229343 | A1 | 12/2003 | Albrecht et al. |
| 2004/0065158 | A1 | 4/2004 | Schrepfer et al. |
| 2004/0168692 | A1 | 9/2004 | Fogarty et al. |
| 2004/0254457 | A1 | 12/2004 | Van der Weide |
| 2005/0010131 | A1 | 1/2005 | Burbank et al. |
| 2005/0021019 | A1 | 1/2005 | Hashimshony et al. |
| 2005/0107717 | A1 | 5/2005 | Yamamoto et al. |
| 2005/0119648 | A1 | 6/2005 | Swanson |
| 2005/0159689 | A1 | 7/2005 | Olson |
| 2006/0253107 | A1 | 9/2006 | Hashimshony et al. |
| 2006/0264738 | A1 | 11/2006 | Hashimshony et al. |
| 2007/0032739 | A1 | 8/2007 | Hashimshony et al. |
| 2007/0032747 | A1 | 8/2007 | Hashimshony et al. |
| 2007/0179397 | A1 | 8/2007 | Hashimshony et al. |
| 2007/0255169 | A1 | 11/2007 | Hashimshony et al. |
| 2007/0260156 | A1 | 11/2007 | Hashimshony |
| 2008/0021343 | A1 | 1/2008 | Hashimshony et al. |
| 2008/0039742 | A1 | 2/2008 | Hashimshony et al. |
| 2008/0154090 | A1 | 6/2008 | Hashimshony |
| 2008/0287750 | A1 | 11/2008 | Hashimshony et al. |

FOREIGN PATENT DOCUMENTS

| | | |
|---|---|---|
| DE | 19705260 A1 | 8/1997 |
| DE | 19734978 A1 | 2/1999 |
| EP | 419235 | 3/1991 |
| GB | 01153980 | 3/1968 |
| WO | WO 97/12553 | 4/1997 |
| WO | WO 01/43630 | 6/2001 |
| WO | WO 01/65240 | 7/2001 |

| WO | WO 01/65240 | 9/2001 |
| WO | WO 03/009752 | 2/2003 |
| WO | WO 03/060462 | 7/2003 |
| WO | WO 2005/009200 | 3/2005 |
| WO | WO 2005/089065 | 9/2005 |
| WO | WO 2006/103665 | 5/2006 |
| WO | WO 2006/072947 | 7/2006 |
| WO | WO 2006/092797 | 9/2006 |
| WO | WO 2007/015255 | 2/2007 |
| WO | WO 2007/083310 | 7/2007 |
| WO | WO 2008/132714 | 11/2008 |
| WO | WO 2008/132750 | 11/2008 |

OTHER PUBLICATIONS

Examination Report Dated Feb. 1, 2008 From the Goverment of India, Patent Office Re.: Application No. 668/CHENP/2006.
Examination Report Dated Nov. 18, 2008 From the Government of India, Patent Office Re.: Application No. 668/CHENP/2006.
International Search Report Dated Nov. 27, 2008 From the International Searching Authority Re.: Application No. PCT/IL2008/000406.
Translation of the Notice of Reason for Rejection Dated Oct. 31, 2008 From the Japanese Patent Office Re.: Application No. 2003-560509.
Translation of the Office Action Dated Jul. 27, 2007 From the Patent Office of the People's Republic of China Re.: Application No. 200480027097.X.
Written Opinion Dated Nov. 27, 2008 From the International Searching Authority Re.: Application No. PCT/IL2008/000406.
Brown "A Survey of Image Registration Techniques", ACM Computing Surveys, 24(4): 325-376, 1992.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Misra et al. "Noninvasive Electrical Characterization of Materials at Microwave Frequencies Using an Open-Ended Coaxial Line: Test of an Improved Calibration Technique", IEEE Transactions on Microwave Theory & Techniques, 38(1): 8-13, 1990.
Mosig et al. "Reflection of An Open-Ended Coaxial Line", IEEE Transactions on Instrumentation & Measurement, IM-30(1): 46-51, 1981.
Stuchly et al. "Measurement of Radio Frequency Permittivity of Biological Tissues With an Open-Ended Coaxial Line: Part II-Experimental Results", IEEE Transactions on Microwave Theory & Techniques, MTT-30(1): 87-91, 1982.
Xu et al. "Measurement of Microwave Permittivity Using Open Ended Elliptical Coaxial Probes", IEEE Transactions on Microwave Theory & Techniques, 40(1): 143-150, 1992.
Communication Pursuant to Article 96(2) EPC Dated Aug. 10, 2006 From the European Patent Office Re.: Application No. 02795418.9.
Communication Pursuant to Article 96(2) EPC Dated Jan. 12, 2006 From the European Patent Office Re.: Application No. 02795418.9.
Communication Relating to the Results of the Partial International Search Dated Sep. 1, 2008 From the International Searching Authority Re.: Application No. PCT/IL2008/000406.
International Preliminary Report on Patentability Dated Feb. 4, 2008 From the International Preliminary Examining Authority Re.: Application No. PCT/IL06/00392.
International Preliminary Report on Patentability Dated Jan. 22, 2009 From the International Bureau of WIPO Re.: Application No. PCT/IL2006/000908.
International Preliminary Report on Patentability Dated Apr. 26, 2007 From the International Bureau of WIPO Re.: Application No. PCT/IL2005/000330.
International Preliminary Report on Patentatbility Dated Aug. 9, 2007 From the International Bureau of WIPO Re.: Applicaiton No. PCT/IL2006/000015.
Office Action Dated Nov. 18, 2008 From the Government of India, Patent Office Re.: Application No. 668/CHENP/2006.
Office Action Dated Mar. 20, 2009 From the State Intellectual Property Office of the People's Republic of China Re.: Application No. 200680019026.4.

Official Action Dated Apr. 1, 2008 From US Patent and Trademark Office Re.: U.S. Appl. No. 11/745,334.
Official Action Dated Jun. 3, 2005 From the US Patent and Trademark Office Re.: U.S. Appl. No. 10/891,750.
Official Action Dated Jun. 4, 2007 From the US Patent and Trademark Office Re.: U.S. Appl. No. 10/298,196.
Official Action Dated Jul. 9, 2008 From the US Patent and Trademark Office Re.: U.S. Appl. No. 11/196,732.
Official Action Dated Apr. 10, 2006 From the US Patent and Trademark Office Re.: U.S. Appl. No. 10/965,752.
Official Action Dated Feb. 10, 2006 From the US Patent and Trademark Office Re.: U.S. Appl. No. 10/298,196.
Official Action Dated Oct. 10, 2006 From the US Patent and Trademark Office Re.: U.S. Appl. No. 10/298,196.
Official Action Dated Nov. 19, 2007 From the US Patent and Trademark Office Re.: U.S. Appl. No. 11/196,732.
Official Action Dated Mar. 21, 2008 From the US Patent and Trademark Office Re.: U.S. Appl. No. 10/558,831.
Official Action Dated Jan. 24, 2008 From the US Patent and Trademark Office Re.: U.S. Appl. No. 10/298,196.
Response Dated Aug. 3, 2007 to Written Opinion of May 3, 2007 From the International Searching Authority Re.: Application No. PCT/IL06/00392.
Response Dated Jan. 4, 2007 to Communication-Pursuant to Article 96(2) of Aug. 10, 2006 From the European Patent Office Re.: Application No. 02795418.9.
Response Dated Mar. 16, 2007 to Communication Pursuant to Article 96(2) EPC of Jan. 19, 2007 From the European Patent Office Re.: Application No. 02795418.9.
Rajshekhar "Continuous Impedence Monitoring During CT-Guided Stereotactic Surgery: Relative Value in Cystic and Solid Lesions", British Journal of Neurosurgery, 6: 439-444, 1992.
Misra et al. "Noninvasive Electrical Characterization of Materials at Microwave Frequencies Using an Open-Ended Coaxial Line: Test of an Improved Calibration Technique", IEEE Transactions on Microwave Theory & Techniques, 38(1): 8-13, 1990.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Xu et al. "Measurement of Microwave Permittivity Using Open Ended Elliptical Coaxial Probes", IEEE Transactions on Microwave Theory & Techniques, 40(1): 143-150, 1992.
Stuchly et al. "Measurement of Radio Frequency Permittivity of Biological Tissues With an Open-Ended Coaxial Line: Part II-Experimental Results", IEEE Transactions on Microwave Theory & Techniques, MTT-30(1): 87-91, 1982.
Mosig et al. "Reflection of an Open-Ended Coaxial Line", IEEE Transactions on Instrumentation & Measurement, IM-30(1): 46-51, 1981.
Brown "A Survey of Image Registration Techniques", ACM Computing Surveys, 24(4): 325-376, 1992.
Smith et al. "In Vivo Measurement of Tumor Conductiveness With the Magnetic Bioimpedance Method", IEEE Transactions on Biomedical Engineering, 47(10): 1403-1405, 2000.
Schwan "Mechanism Responsible for Electrical Properties of Tissues and Cell Suspensions", Medical Process Through Technology, 19: 163-165, 1993.
Surowiec et al. "Dielectric Properties of Breast Carcinoma and the Surrounding Tissues", IEEE Transactions on Biomedical Engineering, 35(4): 257-263, 1988.
Supplementary European Search Report and the European Search Opinion Dated Jun. 5, 2009 From the European Patent Office Re.: Application No. 06728196.4.
Communication Pursuant to Article 94(3) EPC Dated Oct. 7, 2009 From the European Patent Office Re.: Application No. 06728196.4.
International Preliminary Report on Patentability Dated Nov. 12, 2009 From the International Bureau of WIPO Re.: Application No. PCT/IL2008/000406.
Official Action Dated Aug. 27, 2009 From the US Patent and Trademark Office Re.: U.S. Appl. No. 11/705,143.
Official Action Dated Aug. 27, 2009 From the US Patent and Trademark Office Re.: U.S. Appl. No. 11/797,167.

Official Action Dated Aug. 31, 2009 From the US Patent and Trademark Office Re.: U.S. Appl. No. 11/797,166.

Response Dated Oct. 13, 2009 to Official Action of Sep. 15, 2009 From the US Patent and Trademark Office Re.: U.S. Appl. No. 11/196,732.

Response Dated Oct. 13, 2009 to Official Action of Dec. 18, 2008 From the US Patent and Trademark Office Re.: U.S. Appl. No. 10/534,544.

Response Dated Nov. 25, 2009 to Official Action of Aug. 27, 2009 From the US Patent and Trademark Office Re.: U.S. Appl. No. 11/705,143.

Response Dated Nov. 25, 2009 to Official Action of Aug. 27, 2009 From the US Patent and Trademark Office Re.: U.S. Appl. No. 11/797,167.

Supplementary Partial European Search Report and the European Searching Opinion Dated Dec. 4, 2009 From the European Patent Office Re.: Application No. 06700052.1.

Translation of Office Action Dated Sep. 18, 2009 From the State Intellectual Property Office of the People's Republic of China Re.: Application No. 200680006513.7.

Communication Pursuant to Article 94(3) EPC Dated Mar. 15, 2010 From the European Patent Office Re.: Application No. 06700052.1.

Notice of Allowance Dated Oct. 20, 2006 From the US Patent and Trademark Office Re.: U.S. Appl. No. 10/965,752.

Office Action Dated Feb. 11, 2009 From the Israeli Patent Office Re.: Application No. 173231 and Its Translation Into English.

Official Action Dated Feb. 4, 2010 From the US Patent and Trademark Office Re.: U.S. Appl. No. 11/196,732.

Official Action Dated Mar. 11, 2010 From the US Patent and Trademark Office Re.: U.S. Appl. No. 11/797,166.

Official Action Dated Mar. 16, 2010 From the US Patent and Trademark Office Re.: U.S. Appl. No. 11/887,571.

Official Action Dated Mar. 17, 1010 From the US Patent and Trademark Office Re.: U.S. Appl. No. 10/567,581.

Response Dated Jan. 3, 2010 to Office Action of Sep. 18, 2009 From the State Intellectual Property Office of the People's Republic of China Re.: Application No. 200680006513.7.

Response Dated Jan. 7, 2010 to Official Action of Dec. 7, 2009 From the US Patent and Trademark Office Re.: U.S. Appl. No. 11/797,167.

Response Dated Feb. 8, 2010 to Communication Pursuant to Article 94(3) EPC of Oct. 7, 2009 From the European Patent Office Re.: Application No. 06728196.4.

Response Dated Dec. 30, 2009 to Official Action of Aug. 31, 2009 From the US Patent and Trademark Office Re.: U.S. Appl. No. 11/797,166.

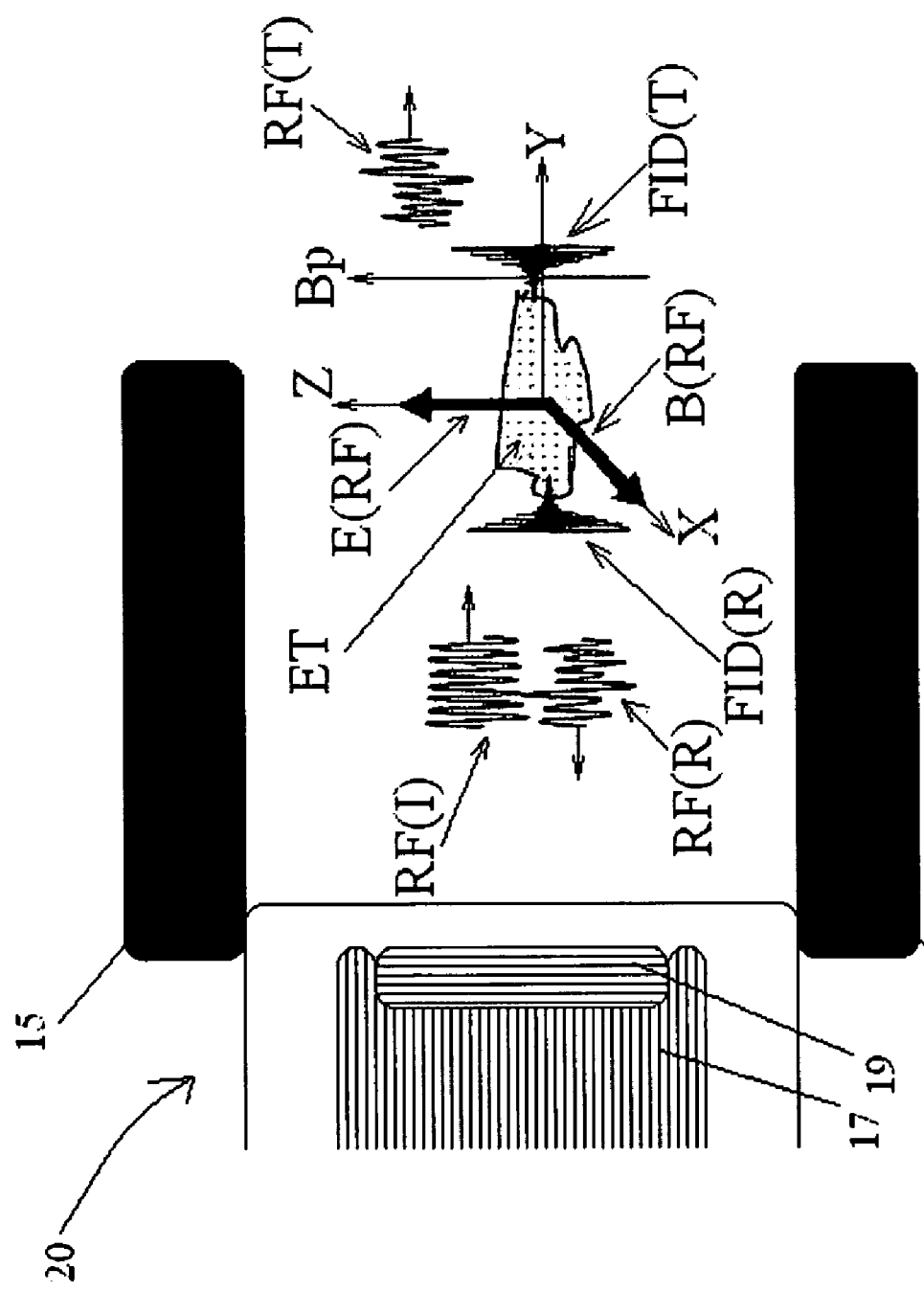

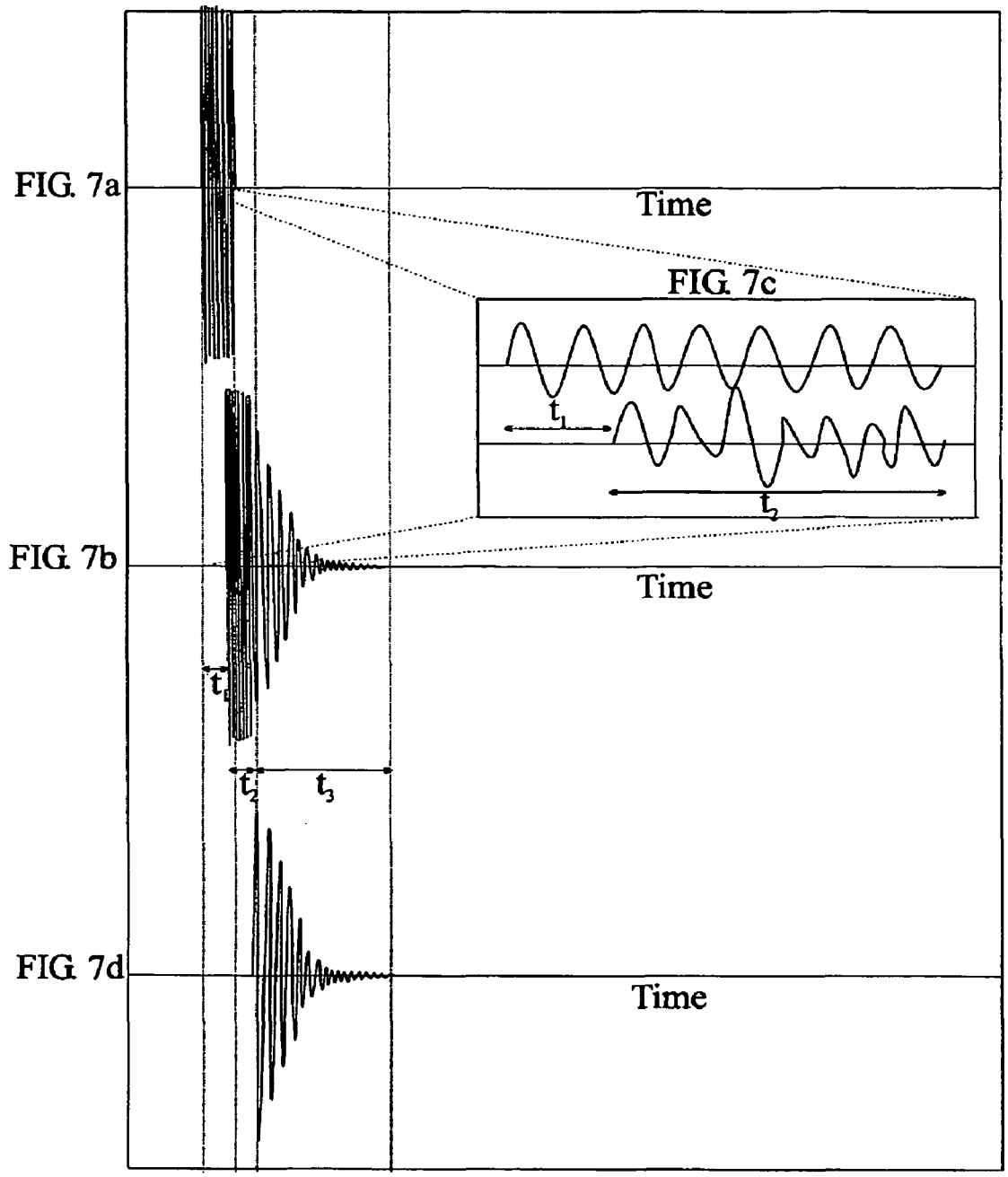

METHOD AND APPARATUS FOR EXAMINING A SUBSTANCE, PARTICULARLY TISSUE, TO CHARACTERIZE ITS TYPE

CROSS REFERENCE TO RELATED APPLICATIONS

This application is a continuation-in-part of U.S. patent application Ser. No. 10/891,750, filed on Jul. 15, 2004, now U.S. Pat. No. 7,082,325 which claims the benefit of U.S. Provisional Patent Application No. 60/481,130, filed on Jul. 24, 2003, the contents of which are incorporated by reference as if fully set forth herein.

FIELD AND BACKGROUND OF THE INVENTION

The present invention relates to a method and apparatus for examining a substance to characterize its type and composition. The invention is particularly useful for examining tissue in order to characterize it as cancerous or non-cancerous, and the invention is therefore described below with respect to this application.

Today, in many surgical applications there is a need to cut biological tissues of a specific type while avoiding cutting tissues of other types. For example, in a tumor removal surgery, the surgeon attempts to cut around the tumor in order to remove it. There are many ways to perform this medical procedure but all share the same fundamental principle: Never cut through a tumor. This principle is the core of good practice and markedly affects the success rate of tumor removal procedures. Failing to keep this fundamental rule increases the failure rate of the surgery, the reoccurrence rate of the cancer, and the rate of necessary re-excisions.

Nevertheless, during surgery the surgeon does not have (except for his trained eyes and fingers) any real-time indication of the kind of tissue that is being cut. Furthermore, if the surgeon cuts through healthy tissue and then, accidentally, cuts a small portion of a malignant tissue, this will be noticed, if at all, only in the pathologist report after conducting a biopsy. Therefore, from the point of view of organ conservation and reoccurrence rate reduction, it is highly desirable to use a real time tool that displays the type of tissue being cut and alerts the surgeon whenever a tumor is about to be cut.

In many medical procedures, the diagnostics tool and surgical assist tools are serially applied to the patient in order to increase the specificity and sensitivity of the tests. When trying to perform such serial examinations during surgical operations, the problem of coordinate registration becomes a crucial one. Therefore, a tool that enables simultaneous measurement of multiple, independent tissue characterization modalities in the same place (i.e. of the same biological mass) possess an added and synergetic value.

There are numerous modalities, methods and devices that have been developed in order to differentiate and characterize tissue as being malignant or healthy. Still, use of multi-modality tissue sensing and characterization probes, as described, for example, in U.S. Pat. No. 6,109,270 and US 20030045798, has the possibility of enhancing the differentiation capabilities of the device.

The ability of detect cancer cells, and especially breast cancer, using electric impedance of tissue is well established in the biomedical literature[1,2,3,4]. Another technique, based on magnetic bioimpedance[5], measures the bioimpedance by magnetic induction. Although the exact mechanism responsible for tissue impedance at various frequencies is not completely understood, the general mechanism[6,7] is well explained by semi-empirical models that are supported by experiments[8,9,10].

Variations in electrical impedance of the human tissue are used in, for example U.S. Pat. No. 4,291,708 and U.S. Pat. No. 4,458,694, to provide indications of tumors, lesions and other abnormalities. Millimeter and microwave devices are used, for example in U.S. Pat. No. 5,807,257, U.S. Pat. No. 5,704,355 and U.S. Pat. No. 6,061,589, to measure bioimpedance and to detect abnormal tissue. Additionally, commonly owned U.S. Pat. No. 6,813,515 discloses a method and apparatus for locally characterizing tissue by its Electric Impedance properties.

MRI has long been recognized as a useful modality/method for tissue characterization as malignant or healthy. MRI is "global" method, which requires positioning of the patient within the apparatus, and is therefore not suitable for use during an operation procedure. Variations of the MRI modality which provide a local MRI probe have been disclosed, for example, in U.S. Pat. No. 5,572,132 where a MRI response is detected in an intravascular device, in WO0239132 where a variation of the intravascular approach is presented, and in U.S. Pat. No. 6,489,767, where a local MRI surface characterization method is disclosed Motion is another problem in any real time imaging or detection tool, such as Magnetic Resonance Imaging (MRI), that demands stationary objects for good imaging results. For example, during breast surgery, the movement of the breast with breathing is a major problem for achieving good resolution. An in situ miniature real-time tool that moves with the body avoids the motion problem. When such a detection tool also possesses an in-situ marking capability, the problem of coordinate registration is substantially eliminated.

SUMMARY OF THE PRESENT INVENTION

The present invention successfully addresses the shortcomings of the presently known configurations by providing a method and apparatus for examining a substance of a given volume to characterize its type, using an integrated sensing head. The method comprises applying locally to the substance of the given volume a polarizing magnetic field, with a component defining a polarizing axis; applying locally RF pulses to the substance of the given volume, the RF pulses having a B component, orthogonal to the polarizing axis, such as to invoke EI response signals corresponding to the electrical impedance (EI) of the examined substance of the given volume, and magnetic resonance (MR) response signals corresponding to the MR properties of the examined substance of the given volume; detecting locally EI response signals from the substance of the given volume; and detecting locally MR response signals from the substance of the given volume. Two or more sensing heads may be used, both applying locally the RF pulses and detecting. Alternatively, one of the sensing heads may operate as a transmitter, while the other or others may operate as receivers.

The present invention relates to multi-modality sensing approach, namely on multi-modality sensing and detection of electric impedance (EI) and magnetic resonance (MR) properties. Preferably, the sensors are integrated into one sensing head, and the modalities are synergistically combined so that a third modality is produced. The method thus utilizes the simultaneous measurement of EI properties of a specific region of the examined tissue (or other substance), combined with the measurement of MR properties of the same region of tissue. The third synergetic mode if utilized, relies on the induced change in the EI properties due to the MR absorption of the incident electromagnetic radiation pulse.

The MR response of the tissue probed can result from two general types/classes of microscopic spins: electronic and nuclear. Electronic spins are from paramagnetic species/molecules/atoms having a non-zero spin due to their electron configuration. This type of response is known in the literature as Electron Magnetic Resonance (EMR), or Electron Spin Resonance (ESR), or Electron Paramagnetic Resonance (EPR). Nuclear spins are from atoms with a non-zero nuclear magnetic moment. This type of response is known in the literature as Nuclear Magnetic Resonance (NMR).

The various MR responses thus include: NMR; EMR, also known as EPR or ESR; Proton Electron Double Resonance (PEDR), also known as Overhauser MR; Longitudinally-detected ESR (LODESR); Field-cycled PEDR (FC-PEDR); and others familiar to those skilled in the art. Various methods are known for detecting these MR responses.

The preferred mode of the invention described below involves detecting NMR properties, more particularly the simultaneous (i.e., within a few seconds) measurement of EI properties of a specific region (voxel) of tissue (or other substance), combined with the measurement of NMR properties from that same voxel. The third synergetic mode, namely the measurement of the induced changes in the EI properties due to the application of the magnetic field for measuring the NMR properties, is preferably also affected in order to enhance the results achievable by the EI and NMR measurements.

While the NMR process is preferred, and is particularly referred to in the description below, the invention may also be implemented by detecting other types of MR properties particularly EMR properties, and with other means for detecting MR responses. However, there are some important differences between the NMR and EMR processes, including the following:

1. EMR probes completely different tissue parameters/states than NMR probes, including metabolism rates, pH, NO concentration, free radicals, reactive oxygen species, and oxygenation state.
2. EMR is usually preformed in conjugation with contrasting agents. These are spin-trap molecules that stabilize the paramagnetic species.
3. The polarizing magnetic fields used in EMR are much lower than those used in NMR.

Since the described probe can work up to a few Ghz (at least 5 Ghz), it can be used both as an EMR probe and as an NMR probe.

The term "examined substance volume", as used herein, refers to the volume/part of the substance which is examined for (1) electrical impedance (EI) response properties, and (2) magnetic resonance (MR) response properties during one measurement process. This examined substance volume is in the range of about 0.2 $mm^3$ to 8000 $mm^3$. The total examined substance generally consists of many examined substance volumes. The examined substance volume is sometimes also referred to (especially in the magnetic resonance imaging community) as a "voxul".

The term "locally" as used herein, refers to the fact that the polarizing magnetic and electromagnetic fields are applied only to the examined substance volume and its immediate surroundings (no more than about five times the largest dimension of the examined substance volume). Thus, only a negligible amount of the polarizing magnetic and electromagnetic fields are present beyond the immediate surroundings of the examined substance volume, as distinguished from, for example, conventional magnetic resonance imaging (MRI) where both the polarizing fields and the RF pulses are applied to the complete body being imaged.

According to still further features in the described preferred embodiments, the detected EI response signals invoked by the RF pulses are processed to calculate the effective electrical impedance of the examined substance, which calculated electrical impedance is utilized in characterizing the substance type. In addition, the RF pulses invoke MR free induction decay (FID) signals, corresponding to the echoes from excited spins in the examined substance when returning to equilibrium, which FID signals are also detected and utilized in characterizing the substance type.

In one preferred embodiment of the invention described below the RF pulses are applied locally via a transmission line in contact with one side of the examined substance, the RF pulses invoking reflected pulses which are detected and utilized in characterizing the substance type. In another described preferred embodiment, the RF pulses are applied locally via a first transmission line which is brought into contact with one side of the examined substance, while a second transmission line is brought into contact with the opposite side of the examined substance, the RF pulses from the first transmission line being transmitted through the examined substance, detected by the second transmission line, and utilized in characterizing the substance type.

According to still further features in the described preferred embodiments, the detected response signals are utilized to characterize the substance type by: analyzing the detected response signals for predetermined parameters characterizing the substance type; and comparing the predetermined parameters with corresponding parameters of known substance types to produce a best match. Preferably, the RF pulses are applied as a sequence of pulses in which some pulses are optimized for EI measurements, and others are optimized for MR measurements.

The detected MR response signals may be analyzed for, for example: spin density, longitudinal relaxation time (T1), and/or transverse relaxation time (T2) of the examined substance.

Preferably, and according to further features in the described preferred embodiments, the detecting of the EI and MR response signals includes: (a) collecting the EI response signals and the MR response signals; (b) analyzing the collected response signals for predetermined parameters characterizing the substance type; (c) modeling the signal parameters into a set of parameters; and (d) classifying the set of parameters according to known parameter sets of known substance types.

According to another aspect of the present invention, there is provided apparatus for examining a substance to characterize its type, comprising: magnetic means for applying locally a polarizing magnetic field through the examined substance volume; and an electrical control and processing system for: (a) applying RF pulses locally to the examined substance volume such as to invoke electrical impedance (EI) response signals corresponding to the electrical impedance of the substance, and magnetic resonance (MR) response signals corresponding to the MR properties of the examined substance volume; (b) detecting the EI and MR response signals; (c) and utilizing the detected response signals for characterizing the substance type.

As indicated earlier, the novel method and apparatus are particularly useful for examining tissue to characterize it as cancerous, or non-cancerous tissue, or partially cancerous tissue.

The advantages achievable by the invention could be further enhanced by adding even more modalities to the EI sensor, by using other, not co-excited modalities, or by combining EI and MR (e.g., NMR) with mechanical and ultrasound impulses. The detection is based on statistical analysis algorithms that compare the measured properties of the tissue investigated to known tissue type properties.

The apparatus may thus be implemented in an external mother unit and a handheld probe connected to it via a flexible transmission line. The hand held probe would include the integrated sensing head, handgrip, and some user controls and indicators.

The invention may be used at the operation table by the surgeon. During an operation, the surgeon would contact the sensing head of the probe with suspicious tissue and receive an immediate indication, based on both electric EI properties and MR properties, whether the contact tissue is cancerous or non-cancerous. Such device could indicate the presence of malignant clusters of cells in the near region (up to about 5-12 mm) from the surface, into the depth of the tissue. This indication would allow the surgeon to achieve the desired clean margin. The device could also include a marking capability that physically marks the tissue at the examination point with the detection results. The simplicity of such an embodiment of the invention would enable its use in a wide variety of tools, especially for tissue recognition during surgical operations.

The apparatus may also be used by the surgeon to perform a scan of the excised section on the operating table, immediately after the section has been removed from the patient's body.

According to other possible embodiments, the probe may also be mounted on a needle to be inserted into the patient's body to perform a biopsy, and to examine the tissue sample, and/or to guide the movement of the biopsy needle during the biopsy procedure. The guiding instructions may be used to assist in the localization of the biopsy needle, and thereby, to prevent the well-known "miss localization of the biopsy site" mistake.

According to yet other embodiments, the probe may also be used in conjunction with a cutting blade or ablation device to perform a real time detection of cancerous tissue followed by immediate local excision.

The probe may also be mounted on the distal tip of a catheter, for example a coronary artery catheter, to be used to identify the tissue and to identify changes in the tissue near the vicinity of the probe. The latter can be very helpful in the case of plaque detection, especially vulnerable plaque, for in-stent re-stenosis inspection, or for general coronary artery inspection.

Another advantage of the presented method is that it can be easily implemented in the form of a single-sided probe, which allows approaching the suspicious tissue from one side only, as is frequently the case during surgical procedures.

In the described preferred embodiments the detection algorithm is based on statistical analysis of the measured parameters, and on identification of similarities between the set of measured parameters and sets of pre-recorded parameters of known tissue types stored in the memory bank of the system. The measured parameters from all modalities are mathematically transformed to an independent parameter set. Thus, by combining information from the different independent modalities of EI and MR, the base for comparison is wider than when using just only one modality. As a result, the probe is capable of providing the surgeon information with superior reliability regarding the type (e.g., cancerous or non-cancerous) of the probed tissue.

Further features and advantages of the invention will be apparent from the description below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings, wherein:

FIG. 2b is a representation of a single sensing head, arranged proximal to the examined tissue, in accordance with embodiments of the present invention;

FIGS. 7a-7d are waveforms helpful in understanding the operation of the apparatus of FIGS. 2-6;

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS OF THE INVENTION

Figure 1:
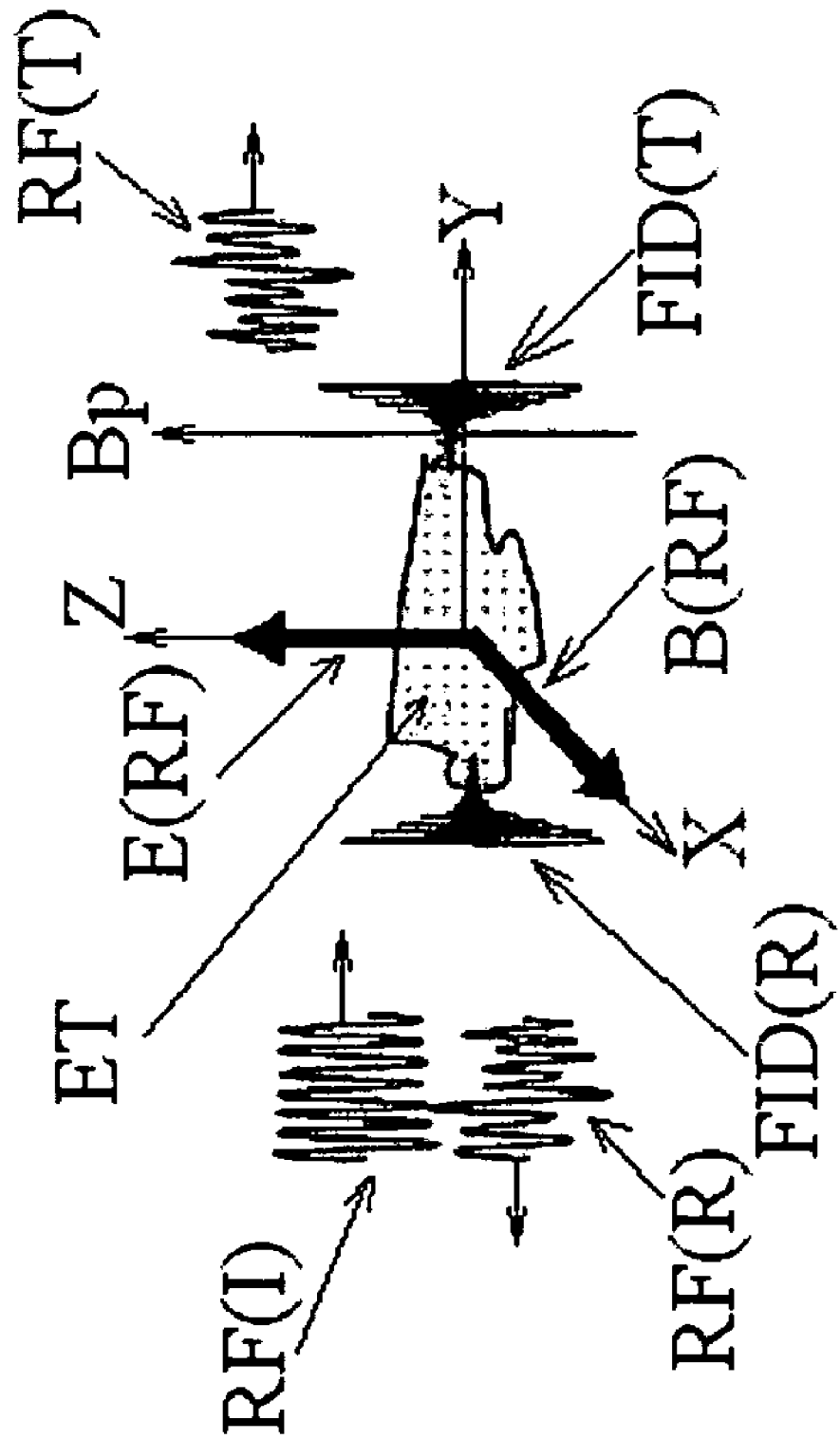
FIG. 1 is a diagram illustrating the basic principle of operation involved in the described preferred embodiment of the present invention.

Basic Principle of Operation (FIG. 1)

Referring now to the drawings, FIG. 1 is a diagram illustrating the basic principle of operation involved in the described preferred embodiment of the present invention.

The basic way by which the present invention realizes the multi-modality approach is by combining EI sensing and MR sensing into one integrated sensing head that collects signals corresponding to both phenomena substantially simultaneously (i.e., within a short, e.g., up to a few seconds) from the same tissue volume (the examined tissue volume). Using the combined modalities sensor, a calculation of the dielectric properties of the examined tissue volume can be derived, as well as the magnetic resonance properties, such as nuclear magnetic resonance properties, known as NMR, and electronic magnetic properties, known as EMR. Furthermore, the change in the dielectric properties of the examined tissue volume induced by the presence of the nuclear spin polarizing magnetic field is also measured, forming a third modality. Tissue characterization or recognition is performed by using algorithms based on statistical analysis of the measured parameters, and by identifying similarities between the set of measured parameters and sets of pre-recorded parameters of known tissue types stored in the memory bank of the system.

The principle of operation can be briefly described by the following operations: application of a constant, or slowly varying polarizing magnetic field to a tissue volume; application of RF electromagnetic fields (while the polarizing magnetic field is applied) to the same tissue volume; and detection of both the EI response signals, the EI response signals being defined as a modification of the incident RF due to the EI properties of the tissue, and MR (such as NMR and EMR) signals from that tissue volume.

The geometry (direction) of the generated polarizing magnetic field must be such that it always has a component perpendicular (orthogonal) to the magnetic field associated with the RF radiation generated in the vicinity of the probe. In the preferred realization, the polarizing field always has a component in the direction of the electric field associated with the RF radiation generated in the vicinity of the probe.

FIG. 1 is a schematic illustration of the presented geometry. As illustrated, the tissue volume examined ET is incident by the RF radiation pulse RF(I) generated by the source and transmitted by the transmission line (TL, FIG. 2a), with that radiation reflected back as a reflected pulse RF(R). When The E-field component $E_{RF}$ of the incident pulse RF(I) is in the Z direction, the B-field (magnetic) component B(RF) of the incident pulse RF(I) is in the direction of the X-axis. Being so, the magnetic field associated with the RF radiation generated by RF(I) in the vicinity of the probe induces a precession of the spins polarized by the external (polarizing) magnetic field Bp, thus generating an NMR Free Induction Decay (FID) signal FID when these spins' direction (the magnetization vector) relaxes back to the polarizing field's direction (the Z-direction in FIG. 1), following the RF pulse RF(I). This NMR signal is further detected simultaneously with the RF reflection response RF(R) of the tissue examined, as part of the RF reflection response RF(R) of the tissue examined. The NMR signal could be detected as an absorption in the reflected spectrum of the RF signal RF(R), followed by the FID signal, in the X-direction in FIG. 1.

It will be appreciated that there are also RF(T) pulses, representing RF pulses transmitted through the tissue ET.

MR signals may similarly be reflected, noted as MR(R), or transmitted, noted as MR(T). Specifically, the Free Induction Decay (FID) signals may be reflected from the tissue ET, represented as FID(R) or transmitted through the tissue ET, represented as FID(T).

The NMR signal could also be detected by an additional magnetic transient field detector, which is perpendicular both to the polarizing magnetic field and the RF excitation related magnetic field so that it is sensitive to magnetic fields in the Y-direction in FIG. 1.

The RF signals RF(I) generated at the end of the transmission line TL can be used according to two modes of operation:

In a first mode of operation, they can be used with pulse duration signals which are much shorter than the time scales related to NMR signals (the spin-lattice relaxation time T1, and the spin-spin relaxation time T2), and which have a repetition rate much higher than the time scales related to NMR signals. In this case the system is viewed as a "continuous wave" NMR system, in the sense that the pumping is effectively continuous, even though the RF radiation, being extremely broadband, will have only a small bandwidth in resonance with the spins.

In a second mode of operation, the incident RF signals RF(I) can be pulses of a length and duty cycle comparable to those used in NMR studies, in which case the system can be viewed as a pulsed NMR system. The relaxation signals are then detected by the TL and/or an additional receiver. This second form of use is the one illustrated in FIG. 1.

For all modes of operation described above, the NMR signal generated could be of the numerous and assorted types of NMR signal known to those skilled in the art. For example, the proton density weighted (PD), the T1 weighted, and the T2 weighted, routinely used in MRI as described for example in Nitz et al "Contrast Mechanisms in MR Imaging", Eur Radiol, 9, 1032-1046 (1999).

The polarizing magnetic field can be modified, and turned on and off, thereby providing a means of measuring the dielectric response of the tissue with various types (including none) of its NMR response. By comparing these responses, the synergistic effect of the modalities is achieved, providing the additional, third modality. The ability to control the polarizing field can also be used to improve dramatically the signal-to noise ratio S/N by using phase locking techniques, by applying a modulation to the polarizing field, for example at 120 Hz. As described more particularly below, this can be achieved, for example, by moving a set of permanent magnets along the Y-direction in FIG. 1, or by changing the location or the driving current in coils, with and without a paramagnetic core. The measurement of the RF reflection is then "locked-on" to this reference frequency and phase.

The TL probe can be of various shapes and types depending on how deep the RF radiation needs to penetrate into the examined tissue. Open cavity ending, open ended, or short ended TL types of ending can be used for generating RF fields only in the near vicinity of the TL, whereupon the range of penetration would be in the order of the diameter of the TL (for coax) or the distance between the strip (for flat lines). Wideband antennas, like a conical antenna, can be used to radiate the energy into the body. The material of which the TL section attached to the permanent magnets should be magnetically transparent.

Generally speaking, the reflection depends on the impedance differences between the continuous section of the TL and its endings. As the ending could be of various types and shapes, its impedance will be correspondingly altered when placed in the close vicinity of the tissue, due to the dielectric properties of the tissue. Accordingly, the reflected pulse carries with it information about the dielectric properties of the examined tissue. These properties produce a change in the time-domain-profile of the reflected pulse. The basic measurement concept is well known and is referred to in the literature on the open-ended transmission line measurement method. A preferred construction is described in International Publication No. WO 03/060462 A2, published Jul. 24, 2003, assigned to the assignee of the present application, the contents of which are incorporated by reference.

The electrical characteristics of the reflected electrical pulse are compared, both in time domain and frequency domain, with those of the applied (incident) electrical pulse by sampling both electrical pulses at a plurality of spaced time intervals, e.g., every 0.2 nanoseconds, and comparing the voltage magnitudes of the two electrical pulses at the spaced time intervals. The reflection coefficient and the time domain filtering properties of the examined tissue are then calculated. The frequency dependent complex impedance of the tissue is then calculated using the theoretical relation between impedance and reflection. The signals are then modeled and reduced into a parameter set that describes and characterizes the tissue measured.

The EI measurement can also be conducted in the transmission mode. In this mode of operation an electrical signal is launched via the transmission line of one probe through the examined tissue and collected by another similar open-ended probe placed on the other side of the tissue. This mode of operation has an advantage from the signal-processing standpoint (although requiring two sided approach and two probes) since the affect of the electrical properties of the tissue on the transmitted signal is stronger then on the reflected signal. This provides a better S/N for the measurement of the tissue properties. This mode of operation is more particularly described below with respect to FIGS. 2c and 12.

The effect of the polarizing magnetic field on the evoked (e.g., reflected) pulses is through the additional absorption of energy from the incident pulse, by the nuclear magnetization vector created due to the presence of the polarizing field. This energy is used to create the precession of the magnetization vector around the direction of the polarizing field. This additional absorption affects the way the electric field is built inside the tissue volume and therefore changes its RF impedance EI. This absorption will appear as a change in the spectrum of the evoked pulse.

A Preferred Construction (FIGS. 2-7)

Figure 2A:
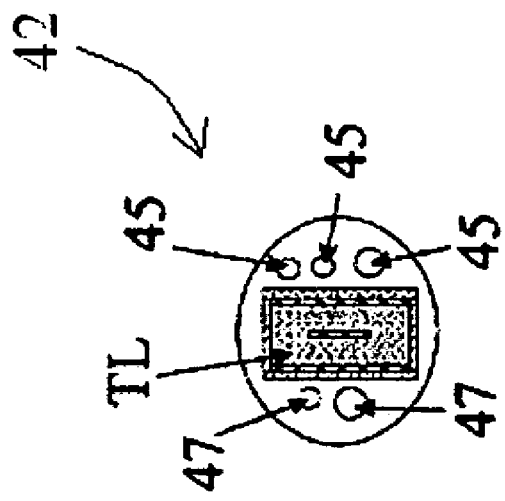
FIG. 2a is a sectional view of FIG. 2 along line a-a.
Figure 2:
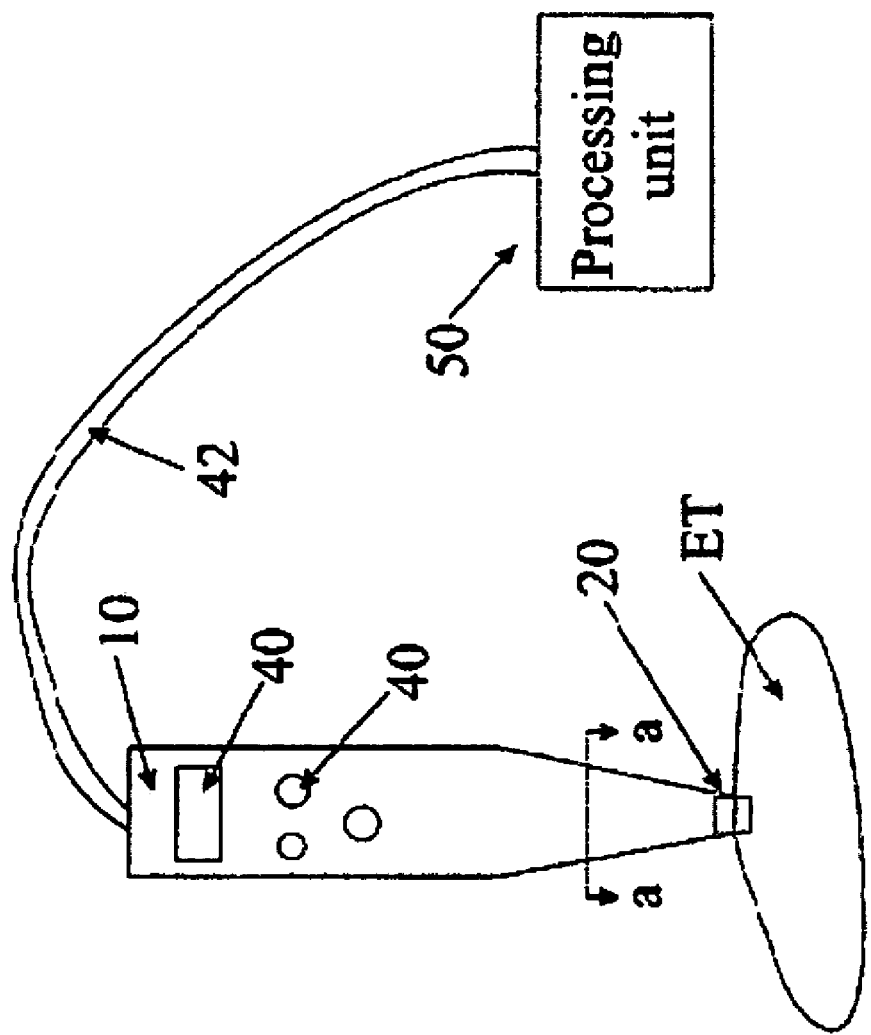
FIG. 2 is a block diagram illustrating one form of apparatus constructed in accordance with the present invention.

Referring further to the drawings, FIG. 2 is a block diagram illustrating one form of apparatus constructed in accordance with embodiments of the present invention, while FIG. 2a is a sectional view of FIG. 2 along line a-a, in accordance with embodiments of the present invention.

FIG. 2 illustrated one form of apparatus, therein generally designated 2, constructed in accordance with the present invention for examining tissue, indicated at ET, to characterize its type, particularly to distinguish cancerous tissue from non-cancerous tissue.

The apparatus illustrated in FIG. 2 includes a multi-modality probe 10 having a sensing head 20 to be placed into contact with the tissue ET to be examined for applying RF(I) pulses via a transmission line TL, and sensing head 20 at the distal end of the transmission line, to the examined tissue. The applied RF(I) pulses are such as to invoke electrical impedance (EI) response signals corresponding to the electrical impedance properties of the examined tissue, and magnetic resonance (MR) response, such as nuclear magnetic resonance (NMR) response signals corresponding to the NMR properties of the examined tissue. Probe 10 is incorporated in a housing which is conveniently graspable by the user for manipulating the sensing head 20. It includes the various controls and indicators, generally designated 40, used to optimize the sensing head 20 performance when applying the RF(I) pulses to the examined tissue ET, and also when detecting the signals evoked from the examined tissue in response to the applied RF(I) pulses. The detected signals are fed to a remotely-located processing unit 50 communicating with the probe unit 10 via a flexible cable set 42, containing the transmission line, additional signal cables and control line cables. Additional signal and control lines 45 (FIG. 2a) and utility lines 47 are also extended through the probe unit 10 up to the sensing head 20.

The probe sensing head 20 in this example is designed to detect both EI reflection signals and MR(R) in RF(R) and MR(R) signals in FID(R) from the tissue ET. Sensing head 20 integrates both modalities and also allows the third synergetic mode to be used. Both types of signals are useful for the identification of various tissue types, such as (but not limited to) normal and cancerous tissue. The measurements are preferably performed in real-time and continuously as the probe is scanned over a tissue section, but may also be performed on the user's demand. The connection between the probe sensing head 20 and the transmission line TL is made as continuous as possible so that the probe sensing head 20 constitutes the distal end of the transmission line TL.

Figure 2C:
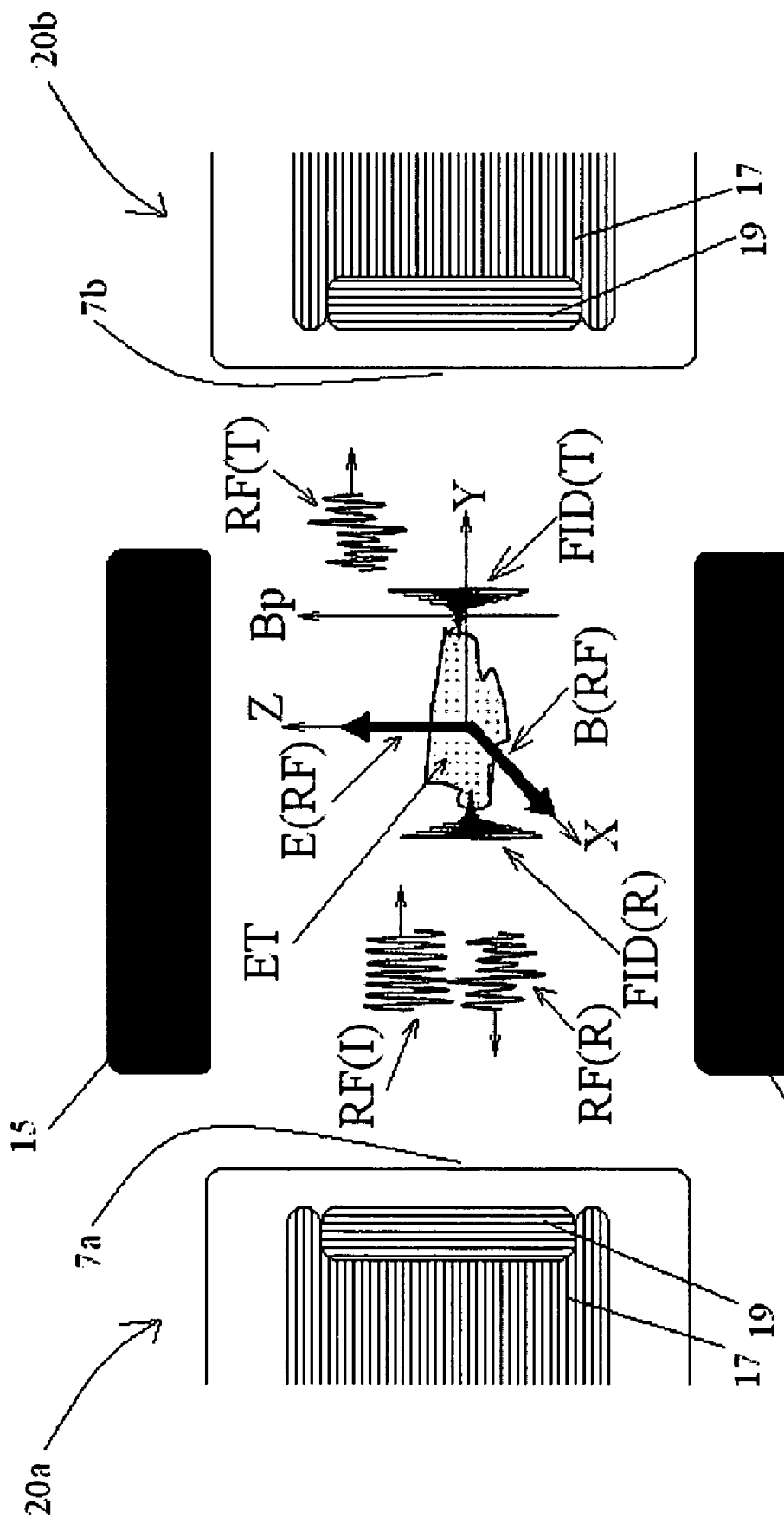
FIG. 2c is a representation of two sensing heads, arranged proximal to the examined tissue, at first and second locations, in accordance with embodiments of the present invention.
Figure 2D:
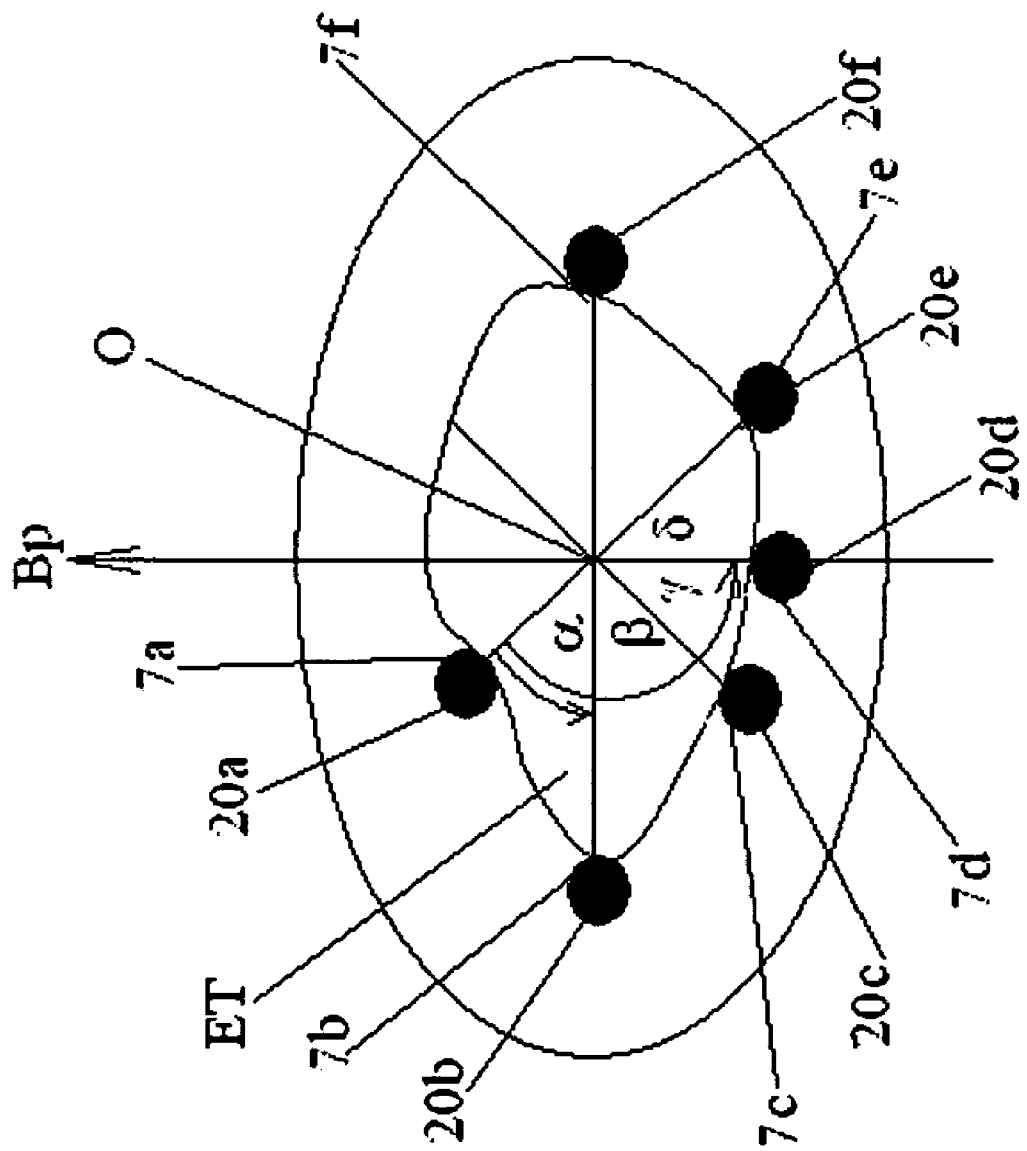
FIG. 2d is a representation of a plurality of sensing heads, arranged proximal to the examined tissue, at a plurality of locations, in accordance with embodiments of the present invention.

Referring further to the drawings, FIGS. 2b-2d are representations of a single sensing head, two sensing heads, and a plurality of sensing heads, respectively, arranged proximal to the examined tissue, in accordance with embodiments of the present invention, As seen in FIG. 2b, the sensing head 20 is arranged proximal to the tissue ET. The sensing head 20 includes the following components:

a. a magnetic-field applicator 15, for applying locally a polarizing magnetic field Bp through the examined tissue ET;
b. a main component 17, which constitutes the open end of the transmission line TL (FIG. 2a), and serves as:
   i. a transmitter of the RF(I) pulses (FIGS. 1 and 2c), for applying locally the RF(I) pulses to the examined tissue ET, the RF pulses having a B(RF) component, orthogonal-to the polarizing axis;
   ii. a receiver of the RF(R) response signals, for detecting locally the EI response signals, which are part of RF(R), reflected from the examined tissue ET; and
   iii. for detecting the MR(R) response signals, which are part of RF(R), whose direction has a component in the direction of the B(RF), and the MR(R) response signals within the portion of the FID(R) reflected signals in the direction of B(RF), for detecting locally the MR response signals reflected from the examined tissue ET; and c. preferably also, an auxiliary component 19, which serves as a receiver of the MR reflected signals, for detecting locally the MR response signals reflected from the examined tissue ET, whose direction has a component orthogonal to B(RF) and orthogonal to the polarizing axis Bp—the portion of the FID(R) reflected signals, whose direction is orthogonal to B(RF) and orthogonal to the polarizing axis Bp.

Alternatively, the magnetic field applicator 15 is an independent unit.

FIG. 2c illustrates first and second sensing heads 20a and 20b, arranged at locations 7a and 7b, respectively, proximal to the tissue. There is a single magnetic field applicator 15 between them, either as an independent unit 15, as shown, or as part of one of the sensing heads, as illustrated in FIG. 2b.

There are two modes of operations for the first and second sensing head arrangement.

In accordance with the first mode, both the sensing heads 20a and 20b operate as follows:
a. applying locally the RF(I) pulses, the RF(I) pulses having their B(RF) component, orthogonal to the polarizing axis;
b. detecting locally the EI response signals; and
c. detecting locally the MR response signals.

However, in this case the EI response signals detected by each of the sensing heads 20a and 20b are derived from both RF(R), reflected from the examined tissue, and RF(T), transmitted through the examined tissue (FIG. 2c), for example, from sensing head 20a to sensing head 20e in FIG. 2d, and vice versa.

Similarly, the MR response signals detected by each of the sensing heads 20a and 20d include both MR(R) response signals, reflected from the examined tissue, and MR(T) response signals, transmitted through the examined tissue (FIG. 2c).

Preferably, concerning the detecting the MR signals, both the sensing heads 20a and 20d are configured for detecting MR(R) and MR(T) whose direction has a component in the direction of B(RF); and MR(R) and MR(T) response signals, whose direction has a component orthogonal to B(RF) and orthogonal to the polarizing axis Bp.

The purpose of this mode is primarily to enhance the strength of the signals.

In accordance with the second mode, one of the sensing heads 20a and 20b operates as a transmitter, for:
a. applying locally the RF(I) pulses, the RF(I) pulses having their B(RF) component, orthogonal to the polarizing axis;
b. detecting locally the EI response signals; and
c. detecting locally the MR response signals.

While the other sensing head operates as a receiver, for:
a. detecting locally the EI response signals; and
b. detecting locally the MR response signals.

Thus the transmitter detects EI response signals, reflected from the examined tissue, and MR(R) response signals, reflected from the examined tissue, while the receiver detects primarily EI response signals, transmitted through the examined tissue, and MR(T) response signals, transmitted through the examined tissue. This situation is illustrated vis a vis FIG. 2c.

It will be appreciated that the first and second sensing heads may alternate between being the transmitter and the receiver, at different times.

The first and the second locations may form an arc of at least 90 degrees vis a vis a centerline of the substance of the given volume or may alternatively form an arc of at least 130 degrees vis a vis a centerline of the substance of the given volume.

FIG. 2d illustrates a plurality of sensing heads 20a-20f, arranged at locations 7a-7f, respectively, proximal to the tissue. There is a single magnetic field applicator 15 between them, either as an independent unit 15 (as shown in FIG. 2c), or as part of one of the sensing heads, as illustrated in FIG. 2b.

Again, there are two modes of operations for the plurality of sensing head arrangement.

In accordance with the first mode, all the sensing heads 20a-20f operate as follows:
a. applying locally the RF(I) pulses, the RF(I) pulses having their B(RF) component, orthogonal to the polarizing axis;
b. detecting locally the EI response signals; and
c. detecting locally the MR response signals.

Again, in this mode, the EI response signals detected by each of the sensing heads 20a-20f include both EI response signals, reflected from the examined tissue, and EI response signals, transmitted through the examined tissue (FIG. 2c).

Similarly, the MR response signals detected by each of the sensing heads 20a-20f include both MR(R) response signals, reflected from the examined tissue, and MR(T) response signals, transmitted through the examined tissue.

The purpose of this mode is primarily to enhance the strength of the signals, even more so than with the two sensing heads of FIG. 2c.

In accordance with the second mode, one of the sensing heads 20a-20f operates as a transmitter, for:
a. applying locally the RF(I) pulses, the RF(I) pulses having their B(RF) component, orthogonal to the polarizing axis;
b. detecting the EI response signals; and
c. detecting the MR response signals.

While all the other sensing heads operate as receivers, for:
a. detecting the EI response signals; and
b. detecting the MR response signals.

The transmitter detects EI response signals, reflected from the examined tissue, and MR(R) response signals, reflected from the examined tissue, while the receivers detect a combination of EI response signals, reflected from the examined tissue, EI response signals, transmitted through the examined tissue, MR(R) response signals, reflected from the examined tissue, and MR(T) response signals, transmitted through the examined tissue.

It will be appreciated that the task of being the transmitter may rotate amongst the sensing heads 20a-20f, each being a transmitter at a time.

Figure 3:
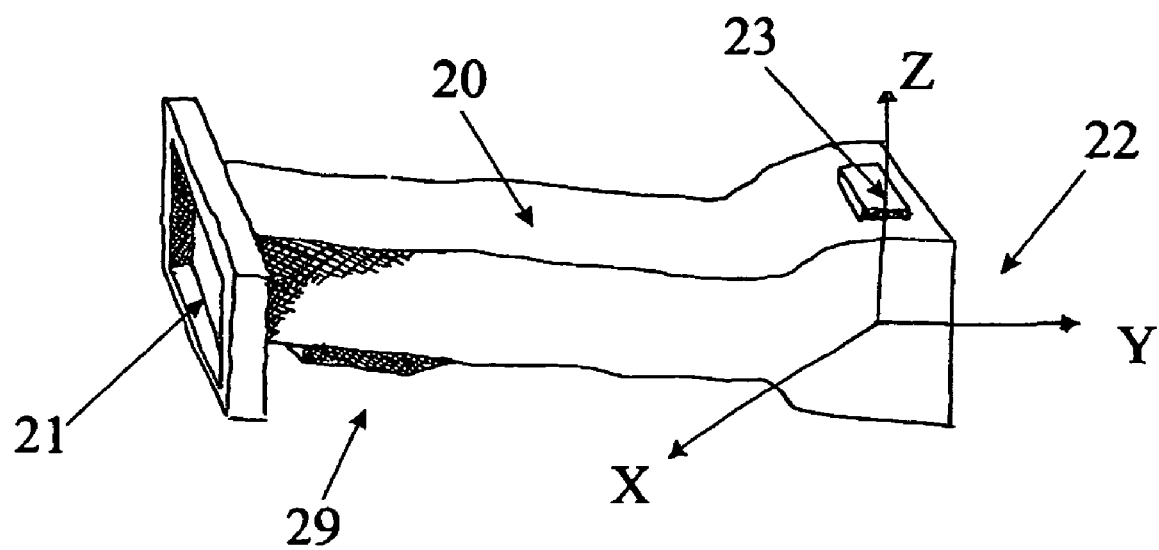
FIG. 3 is a three-dimensional view illustrating the sensing head in the apparatus of FIG. 2.

FIG. 3 illustrates the construction of the probe sensing head 20 and identifies the various axes involved during the operation of the probe as described more particularly below. The proximal end of sensing head 20 includes a connector 21 for connecting it to the transmission line TL so as to constitute the distal end of the transmission line. The distal end 22 of sensing head 20 is adapted to be brought into contact with the tissue to be examined. Also shown in FIG. 3 is a tuning circuit 23 for varying the impedance of the open end of the transmission line defined by the sensing head 20 at the distal end of the transmission line TL.

Figure 3A:
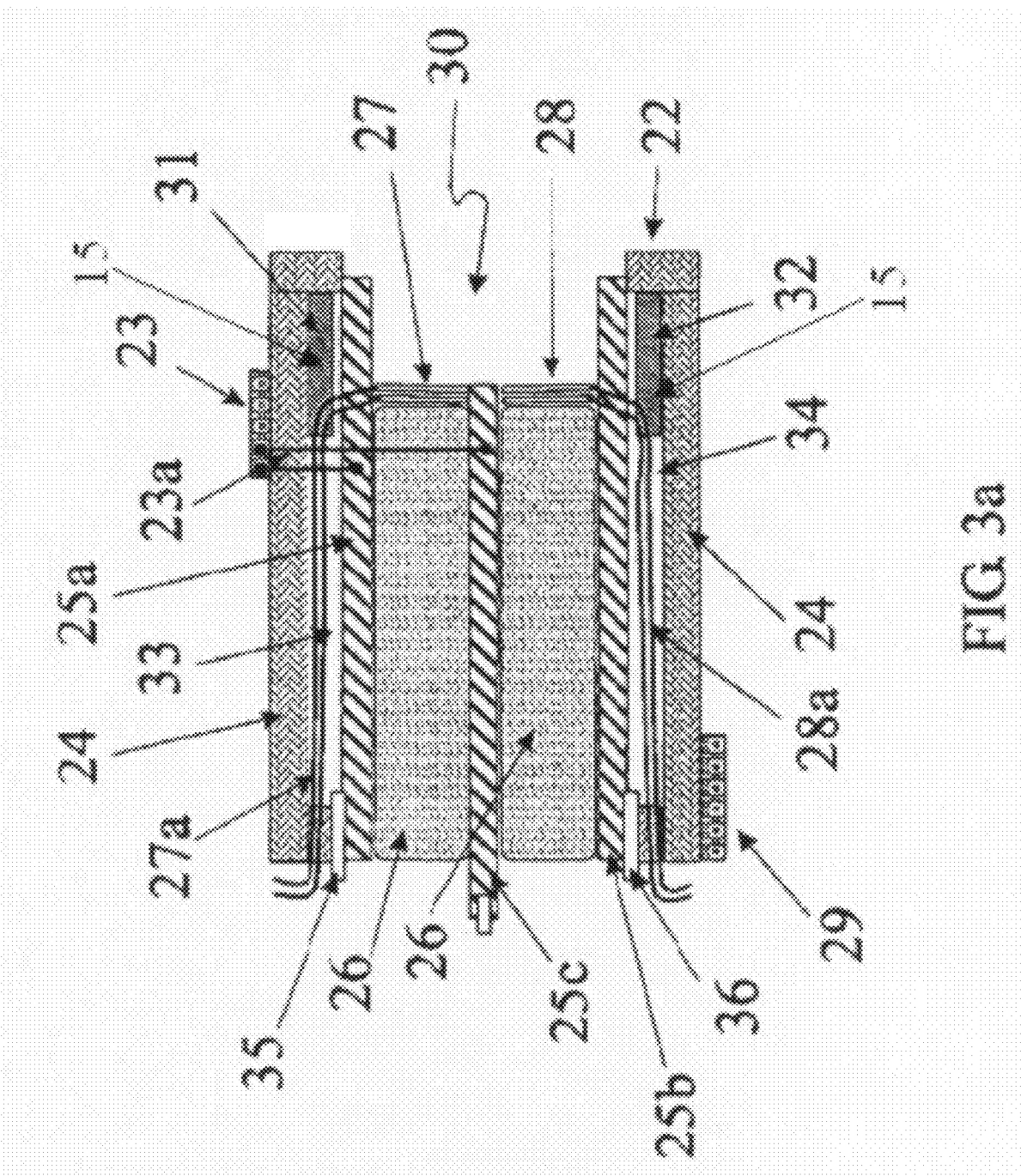
FIGS. 3a and 3b are sectional views of the sensing head in FIG. 3, along the ZY-plane and XZ-plane, respectively.
Figure 3B:
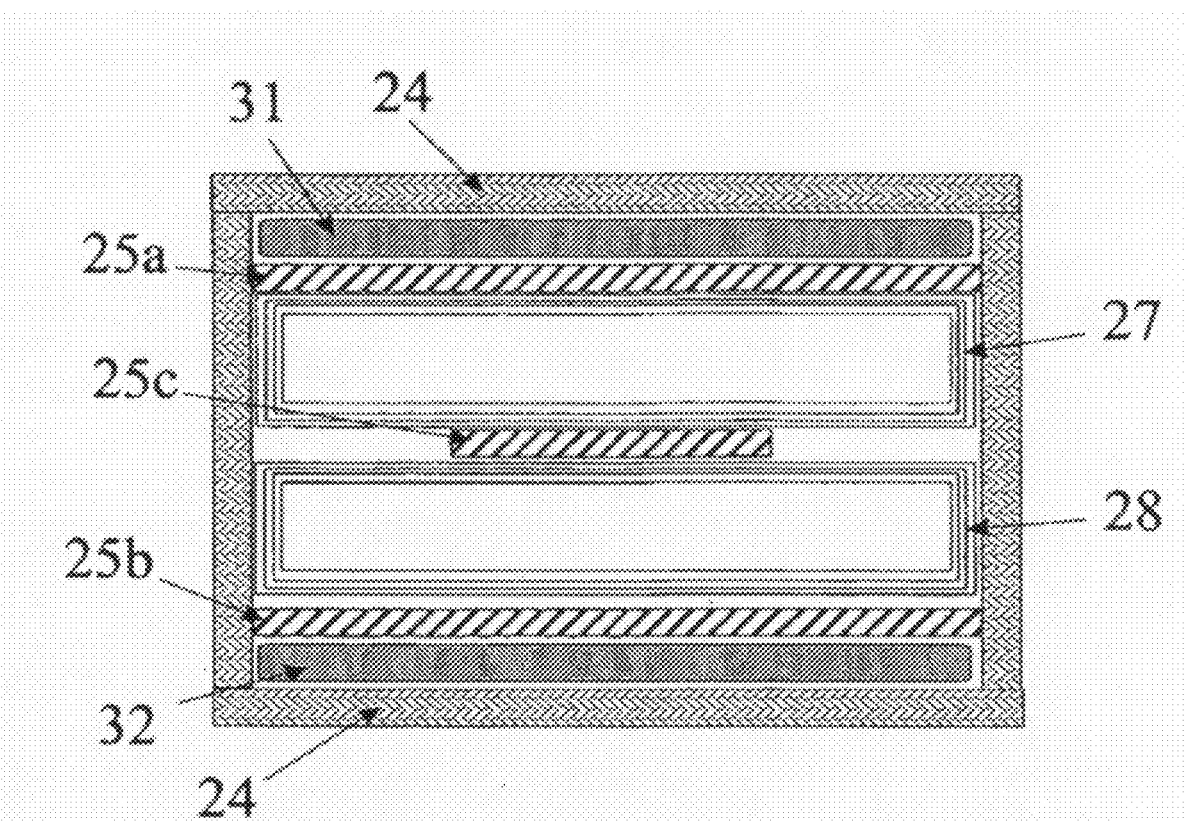

As shown in FIG. 3a, sensing head 20 includes an outer housing 24 containing a transmission line section of the strip-line type, including three conductive strips 25a, 25b, 25c, separated from each other by insulation 26. The two outer conductive strips 25a, 25b constitute the two ground plates of the strip-line, whereas the inner conductive strip 25c constitutes the inner conductor of the strip-line. The ground plates 25a, 25b are made from a magnetically transparent conductive material, e.g., aluminum.

Thus, the main component 17, is formed of elements 25a, 25b, 25c, and 26, while the auxiliary component 19 is formed of elements 27 and 28.

The transmission line defined by sensing head 20 is left open-ended and serves both as a transmitter and a receiver. The open end is connected by wires 23a to the tuning circuit 23. Thus, the impedance of the open ended transmission line can be varied by tuning circuit 23 from zero up to about the open-end impedance. This tuning can be used to increase/decrease the open-ended reflectivity, and to increase/decrease the strength of the B-RF field, that is, the magnetic field generated by the transmission of the RF pulse to the sensing head 20 at the distal end of the transmission line.

As described, for example, in the above-cited International Publication No. WO 03/060462, the outer conductors 25a, 25b and the inner conductor 25c define open cavities closed by the tissue ET being examined, such that when a pulse is transmitted through the transmission line, the pulse is reflected back to the transmission line. The reflection depends on the impedance of the region at the open cavity of the probe, which impedance depends on the dielectric properties of the examined tissue closing the open of the cavity. Accordingly, the reflected pulse carries with it information about the dielectric properties of the examined tissue. These properties produce a change in the time-domain-profile of the reflected pulse.

The transmission line defined by conductors 25a-25c of the sensing head 20 also detect NMR signals evoked in response to the transmitted RF(I) pulses. In the construction illustrated in FIG. 3a, additional NMR signals are detected by a pair of RF coils 27, 28, at the open end of the transmission line defined by conductors 25a-25c, and are outputted from the sensing head 20 via conductors 27a, 28a, respectively extending through the sensing head. The sensing head further includes a small pre-amplifier 29 which serves, together with the tuning circuit 23, in order to improve and to amplify the signals detected by the RF coils 27, 28.

Figure 4:
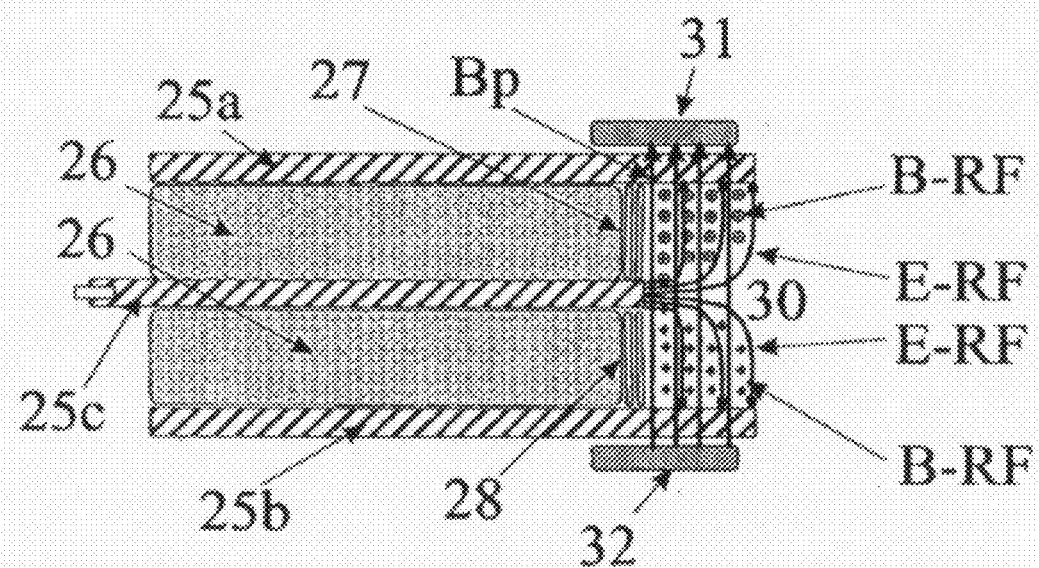
FIG. 4 diagrammatically illustrates the configuration of the electric and magnetic fields produced by the sensing head of FIG. 3.

At the distal end of the probe, there is the magnetic-field applicator 15, for example, formed of two permanent magnets 31, 32 for generating the polarizing magnetic field Bp for aligning the spins of the nuclei in the examined tissue from which NMR signals will be generated. Magnets 31, 32 are designed to generate in region 30 a magnetic field Bp whose major component would be in the direction Z, perpendicular to the B-RF field generated in and near the open cavity. As seen in FIG. 4 the B-RF field has a different direction in the upper section of the sensing head, above the inner conductor 25c, than in the lower section of the sensing head, below the inner conductor 25c. These magnets which may be composed of (but not limited to) rare earth neubidium type magnetic material, may be attached to the outer conductors 25a, 25b with the ability to slide along them in the Y-direction within chambers 33, 34.

The position of magnets 31, 32 can be controlled by air pressure inside the chambers 33, 34 by an external air pump connected thereto via pipes 35, 36. The movement of magnets 31, 32 provides a means for modifying the strength/amplitude of magnetic field Bp in the region 30, while not changing its direction significantly. The magnets' poles (N-S) direction is perpendicular to the probe's main axis (the Y axis). That is, the poles are aligned with the Z-axis.

The transmission line section of the sensing head 20 may be of different types, dimensions, impedances, materials, etc., as long as it kept magnetically transparent in the region where field Bp is generated by the magnets. The ending of the transmission line section can be of various shapes and types depending on how deep the RF radiation is to penetrate into the examined tissue ET. For example, the sensing head can be ended as a wide band antenna, which could be of the type, for example, of a conical antenna in the case of a coax line, or a dipole antenna, or a V-shaped antenna, or a strip line antenna (the two ground strips being opened gradually to the sides) in the case the line is flat. The transmission line can be also left open-ended, or can be ended by a surface coil or by a side emitting leaky end. The preferred way is to form an open cavity at the end of the transmission line and let a small part of the tissue penetrate into the open cavity of the TL. In this way, the RF fields can be considered as with known geometrical configuration (the TL modes) inside the sensing head and near its end, and the RF fields will be transmitted only into a small proximal volume of the tissue, with little radiation transmitted into the remainder of the body.

The additional receiving coils 27, 28 are positioned so that they will detect magnetic fields in a direction perpendicularly to both the Bp and the B-RF magnetic fields. Thus, they will be able to detect the NMR signal in the XZ plane, a direction in which the transmission line TL defined by the conductive strips 25a-25c cannot detect the NMR signals. Their design could be of the types known in the literature, such as: surface coils, single coils, multi-turn coils, saddle coils, etc.

FIG. 4 schematically illustrates the various fields present in the region 30 at the distal end of the transmission line defined by conductive strips 25a-25c. Thus, the substantially homogenous polarizing magnetic field generated by the permanent magnets 31, 32, is shown as magnetic field Bp; the magnetic field generated by the transmission of the RF(I) pulses from the distal end of the transmission line is indicated by magnetic field B-RF which, as indicated earlier, extends in one direction between conductive strips 25c and 25a, and in the opposite direction between conductive strips 25c and 25b; and the electric field generated by the transmission of the RF(I) pulses from the distal end of the transmission line is indicated E-RF. As indicated above, the additional receiving coils 27, 28, when included, serve as additional receivers for detecting the NMR signal components along an axis orthogonal both to $B_P$ (the polarizing magnetic field by the permanent magnets 31, 32), and B-RF (the magnetic field generated by the transmission of the RF(I) pulses from the distal end of the transmission line). Coils 27, 28 are orthogonal to the transmission line main axis (the Y-axis), so that the RF coils 27, 28 detect NMR signals in the Y-direction.

The signal fed into the probe sensing head 20 through the transmission line defined by conductive strips 25a-25c, is of the form of a train of repetitive pulses. The repetitive pulse train, called the RF sequence, consists of combinations of repetitive pulses in which some are optimized for EI measurement, and some are optimized for NMR measurement. The NMR pulses can be, for example, from one of the known (in the literature) NMR sequences. For example, a combined sequence schematically may be as follows: First, an EI optimized set of pulses, e.g., a short nano-second pulse train followed by a time break, in which the reflection is collected with a very high sampling rate. This is followed by an NMR optimized set of pulses; for example, the NMR pulses can be the known inversion recovery, simple spin echo, Carr-Purcell-Meiboom-Gill echo train, stimulated echo, etc.

Figure 5:
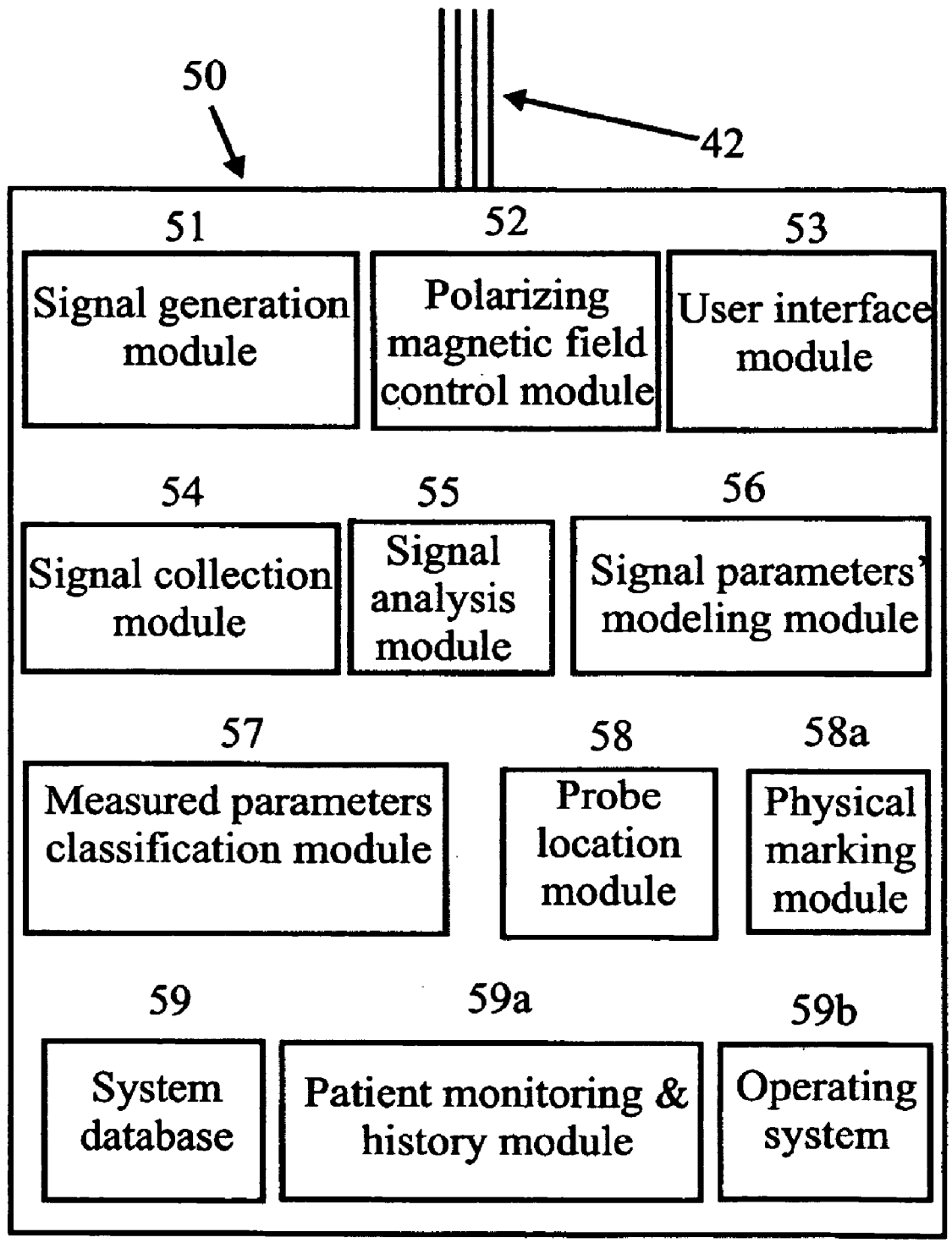
FIG. 5 is a block diagram illustrating the major components or modules in the apparatus of FIGS. 2-4.
Figure 6:
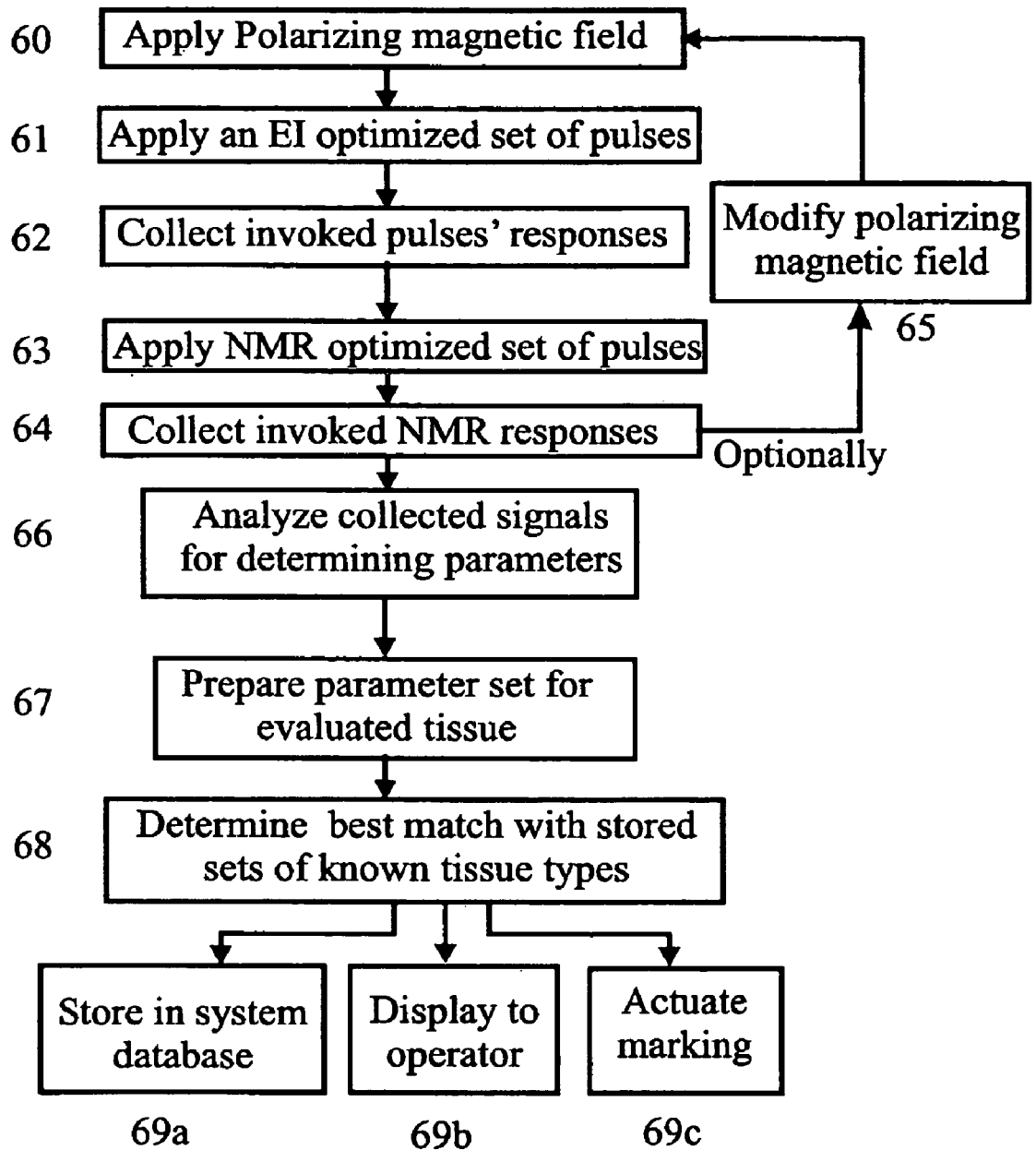
FIG. 6 is a flow chart illustrating a preferred mode of operation of the apparatus of FIGS. 2-5.

FIG. 5 is a block diagram illustrating one form of apparatus constructed and operating in accordance with the present invention as describes above; and FIG. 6 is a flow chart illustrating the operation of such an apparatus when used to examine tissue for distinguishing cancerous tissue from non-cancerous tissue. To facilitate understanding, the block diagram illustrated in FIG. 5 identifies the main components of the apparatus illustrated in FIG. 2 with corresponding reference numerals.

Thus, FIG. 5 illustrates the flexible cable set 42 (which contains the transmission line TL carried by probe 10 and having a distal end occupied by the sensing head 20 adapted to be brought into contact with the tissue to be examined) that connects the probe 10 to the processing unit 50 (FIG. 2). FIG. 5 also illustrates the controls, located within the processing unit 50, for applying and receiving RF pulses via the transmission line TL and sensing head 20 to the examined tissue ET, which pulses are capable of invoking electrical impedance (EI) response signals corresponding to the electrical impedance of the examined tissue, and nuclear magnetic resonance (NMR) response signals corresponding to the NMR properties of the examined tissue. As described above, control circuitry within processing unit 50 also controls the sensing head 20 to detect the EI and NMR response signals, and to feed them via transmission line in flexible cable set 42 to the processing unit 50 for analyzing the detected response signals and for determining therefrom the type of tissue examined, e.g., cancerous or non-cancerous tissue. This determination is indicated to the user by an indicator in probe 10. The determination may also be used to actuate a marker for marking the tissue according to the tissue-type determination.

Thus, as shown in FIG. 5, the controls within the processing unit 50 include a signal generation module 51 capable of generating programmable electric pulses up to 5 GHz; a polarizing magnetic field control module 52 for controlling the polarizing magnetic field (Bp) within region 30 occupied by the examined tissue; and a user interface 53.

The user interface 53 module controls the display unit, an audio unit, optionally a marking unit control, and a control panel. Some of the operation controls and indicators can be mounted on the probe handgrip unit. The main functions of the user interface are to control the operation of the system and to display (in visual and/or audio form) the outputs of the processing unit 50 in a way that will be informative to the user.

The control of the polarizing magnetic field may be effected by changing the position of the permanent magnets 31, 32 (FIG. 3*a*) of the sensing head 20. One way to perform this is by a mechanical push/pull shaft mechanically connected to the magnets and mechanically controlled by control module 52. Another way of moving the magnets is by the use of a vacuum assisted shaft. The magnets are mechanically connected to a short shaft at their remote (relative to the distal end of the probe head) end. The short shaft is connected at its opposite side to an air piston. The air piston is inserted into an air tube that is connected to a pulsed vacuum pump at the external unit side. Each time the air pressure is reduced in the tube, the magnets are pulled back and vice versa.

According to another embodiment of the invention, the polarizing magnetic field would be produced and controlled by electromagnets, in which case the change in the polarizing magnetic field would be effected by a change in the location of, or the current through the coils generating this polarizing field. Another alternative would have the coils surrounding a paramagnetic core, in which case the change in the polarizing magnetic field would be effected by a change in the induced magnetic field in the core due to a change of current in the surrounding coils.

The control and indicator circuitry within the processing unit 50 would further include a signal collection and digitizing module 54 for detecting the excitation RF pulses the reflected RF pulses and the FID NMR pulses. A preferred way of detection is by digitizing voltages along the one or more transmission lines (for example, when one or more sensing heads are employed) using an analog to digital converter module. Preferably the digitizer sampling rate is controlled so as to be able to reach up to twice the signal generator maximal frequency.

The signal collection and digitizing module 54 communicates with a signal analysis module 55. The signal analysis module is a computer program made up of a set of software routines. It receives as an input the measured signals in the form of a set of vectors, and removes noises and artificial effects from the signals. Its output is the set of "clean" processed signals.

As further shown in FIG. 5, the processing unit further includes a signal modeling module 56, a classification module 57, and a data-base module 59.

The signal-modeling module 56 is a computer program, made up of a set of software routines, which calculates a set of parameters that characterize the measured tissue. The data-base module 59 stores a database of various types of tissues and their characterizing set of parameters, including their statistical dispersion properties.

The classification module 57 is a computer program, made up of a set of software routines, which looks for similarities between the measured set of parameters outputted from the modeling module 56, and the pre-recorded set found in the data-base module 59. One simple similarity estimator is the distance of the measured points, in the multi-dimensional parameter data-space, from the location of each one of the prerecorded groups, defining specific tissue types. The most similar group (best-match) defines the type of the examined tissue ET.

The determination of the classification module 57 is outputted via flexible cable set 42 to a tissue characterization indicator 40 within the hand-held probe 10, which displays to the user the determined tissue type.

The processing unit 50 may also include a probe location module 58, and a physical marking module 58*a* controlled by the classification module 57 in the processing unit 50.

Marking module 58*a* controls the operation of marking a measured spot on the tissue by an appropriate physical mark when instructed by the processing unit 50. It uses a detectable material to physically mark the location of measurement. The detection of the marking can be immediate or delayed by the user. The simplest way to perform the marking is by the use of visually detectable substance, e.g., a three color biological marking ink, emitted from a jet nozzle mounted at the tip of the probe. After tissue recognition has been performed, a printing order is sent to the jet nozzle and the appropriate color dot is printed.

Other forms of detectable marking material can be, for example, a physical marker conjugated to antibodies, metal balls, IR paint, etc. The marker can also be a solid marker like a small metal pin, or a combination of solid balls painted with a distinguishing color. The solid balls are palpable and the color is visible. The marker can also be detectable by other known modalities, like X-ray or ultrasound.

As further shown in FIG. 5, processing unit 50 further includes a patient monitoring and history module 59*a*, and an operating system, generally designated 59*b*, namely the computer software that controls and coordinates all the operations of the hardware and software components of the apparatus.

Reference is now made to the flow chart illustrated in FIG. 6 describing the overall operation of the apparatus.

Thus, the user grips probe 10 and brings the sensing head 20 at the distal end of the transmission line TL into contact with tissue ET to be examined. When this contact is established, probe 10 applies a repetitive train of RF pulses, called an RF sequence, through the transmission line, defined by the conductive strips 25*a*-25*c*, which pulses invoke electrical impedance (EI) response signals corresponding to the electrical impedance properties of the examined tissue, and nuclear magnetic resonance (NMR) response signals corresponding to the NMR properties of the examined tissue. As indicated above, the RF sequence of pulses consists of some pulses optimized for EI measurement and other pulses optimized for NMR measurement. The response signals evoked by the applied sequence of RF pulses are detected by the sensing head 20 and processed by the processing unit 50 to determine the type of tissue examined.

The foregoing operations are briefly illustrated in the flow chart of FIG. 6. Thus, as shown in FIG. 6, the system first sets a polarizing magnetic field (block 60). The system then applies an EI optimized set of pulses to the examined tissue (block 61) and collects the invoked pulse responses (block 62), which in this case would be reflected pulses reflected from the open end of the transmission line TL. The system also applies an NMR optimized set of pulses (block 63) to the tissue, and collects therefrom the NMR responses (block 64). The detected response signals would thus provide information as to two modalities of the examined tissue, namely its EI properties and its NMR properties.

Optionally, to provide better information concerning a third modality of the examined tissue, the polarizing magnetic field (Bp), produced by the permanent magnets 31, 32 is modified as described above (block 65), and the operations of blocks 60-64 are repeated to obtain the corresponding information when the examined tissue is subjected to the modified polarizing magnetic field.

The signals collected in the above-described operations are analyzed for predetermined parameters (block 66), and a parameter set is prepared for the examined tissue (block 67). The parameter set prepared for the respective examined tissue is then compared with stored parameter sets of known tissue types as described above, and a best-match determination is made to identify the type of the examined tissue (block 68).

It will thus be seen that the detection process is comprised of the following four operations: (1) signal collection/acquisition; (2) signal analysis; (3) signal parameters' modeling; and (4) classification of measured parameter set to known tissue type parameter set, prerecorded and saved in the memory bank of the system.

The collection of the signals is made by fast digitizing, using multiple acquisition channels. The analysis is made by the application of signal processing routines that clean the signals from noise and artificial affects.

The modeling is made by a compression process that characterizes a signal by a relatively short array of parameters, and mathematically transforms the parameters to an orthogonal set of parameters. For example, a 10000 point acquired signal can be characterizes by an array 10 of parameters. The modeling is done both in the frequency domain and in the time domain.

The classification is performed by a best-match comparison of the measured parameters to known tissue parameters stored in the memory together with their statistical dispersion parameters, and by identification of similarities between the just measured parameter set and a specific tissue type group of parameters.

Following this comparison, the just examined tissue type is characterized, and that information is, for example, stored in the system data-base (block 69a), displayed to the operator (block 69b), used to actuate a marker to mark the tissue (block 69c), or used in any other way needed, according to the specific procedure performed.

FIGS. 7a-7d provide schematic illustrations of the synergistic EI response and NMR response of the examined tissue following the irradiation by a single pulse generated by the main unit's signal generator.

FIG. 7a shows the form of the excitation pulse generated. In this example it is a pulse of the length of a few tens of microseconds, which will invoke both an EI response and an NMR response. It is a pulse of the so-called 90 degree pulse type, know in the NMR literature.

FIG. 7b shows the response of the tissue to the excitation pulse shown in FIG. 7a detected by sensing head 20 in the TL. The response is delayed by a time interval $t_1$ due to the length of the TL, and is composed of two types of signals. The first (temporal) part, in time interval $t_2$, is the EI response of the tissue, which "follows" the form of the excitation pulse in FIG. 7a, but distorts it because of the frequency-dependent dielectric properties of the tissue and the absorption by the nuclear magnetization vector. The second part in time interval $t_3$ is the free induction decay (FID) of the NMR signal generated by the relaxation of the nuclear spin magnetization vector in the examined tissue (region 30, FIG. 3a) back to the direction of the Bp field (see FIG. 4), following the "excitation" by the "90 degree" pulse in FIG. 7a. FIG. 7c shows a close up view of the signal in time interval $t_1$ and $t_2$. In this time segment, the reflected EI pulse is similar to the incident pulse, but is distorted because of the tissue impedance and NMR absorption.

In FIG. 7d is shown the response of the tissue to the excitation pulse shown in FIG. 7a, detected by the RF coils 27, 28. In this channel, the response is composed only of the FID of the NMR signal generated due to the relaxation of the nuclear spin magnetization vector in the examined tissue in region 30 back to the direction of the Bp field (see FIG. 4) following the excitation by the excitation pulse in FIG. 7a. It is to be noted that, since the directions of detection (with regards to the NMR signal) of the coils is orthogonal to that of the transmission line TL, the FID response is phase-shifted by 90 degrees relative to the FID signal detected by the transmission line TL (see FIG. 7b).

The transmitted radiation's spectrum is determined by the form of the pulse, and by the design of the sensor. The spatial form of the radiation (lobe structure, etc.) is determined by the geometry of the sensing head 20 at the distal end of the transmission line TL. Since the examined tissue is in close proximity to the distal end of the transmission line, pulses reflected back into the transmission line because of the impedance differences between the tissue and distal end of the transmission line, provide direct information regarding the dielectric properties/response of the tissue. These are the signals in time interval $t_2$ in FIGS. 7b-7d. The pulse form, duration, repetition, and sequence structure, are designed, and are also controlled in real time, so that they will provide the maximal (S/N) resolution for differentiating between different types of tissue.

As indicated earlier, the tissue measurement is based on a comparison of the incident pulse to the reflected pulse, and on the analysis of the FID, and results in a series of parameters characterizing the tissue; whereas the detection of cancerous tissue sections is based on the comparison of the, just measured, tissue parameters with the parameters defining various tissue types stored in the memory bank.

The external polarizing magnetic field (Bp) generated by the magnets 31, 32, aligns the spins, and particularly nuclear spins of the nuclei (preferably proton/hydrogen) parallel to the aligning magnetic field lines. This generates a "nuclear magnetization vector" in the tissue volume 30. The geometric orientation of the transmission-line transmitted RF pulses is such (see also FIG. 4) that these RF pulses serve as an RF "deflecting" magnetic field for the "nuclear magnetization vector", as is performed in numerous NMR procedures and set-ups.

The NMR FID following the relaxation of the magnetization vector, which follows after the RF pulse has been transmitted, is detected by the sensing head 20, providing detection of the NMR response of the tissue. The RF energy absorbed by the magnetization vector, as it is rotated during the RF pulse duration, is also detected, as a change in the spectrum of the dielectric response of the tissue examined.

Additionally, but not necessarily, the RF receiving coils 27, 28 (FIG. 3*a*) detect the NMR FID signal components in the direction perpendicular to the transmission line TL receiving direction. This measurement provides additional information and a better signal-to-noise ratio, and is correlated with the NMR signals detected by the transmission line. This will improve the NMR signal detection abilities and sensitivity of the probe.

The NMR response of the tissue is detected in three different ways by the system: 1) as an absorbance in the reflected RF pulse contributing to the effective calculated impedance; 2) as an FID following the RF reflected pulse; and 3) as an FID detected by the RF coils 27, 28. The significant NMR measured tissue parameters are, but not limited to proton density (PD), longitudinal relaxation time (T1) and/or transverse relaxation time (T2).

The magnetic fields generated by the magnets 31, 32 may have a gradient in the Y direction (the direction along the probe axis). This will shorten the duration of the NMR response and weaken the signal due to NMR line broadening. The pulse sequence is designed to take these issues into account. Alternatively (not shown), the magnets could be arranged in a form that will minimize the gradient in the Y-direction (the direction along the probe axis) of the field generated by the magnets. The pulse sequence would then be designed differently from the case when there is a significant gradient in the field, in order to obtain the best SNR for the NMR signal.

As described above, the magnets 31, 32 generating the Bp may also be moved during the measurement process. The movement is in the Y direction (the direction parallel to the probe axis). This movement will generate changes in the amplitude, and may also generate slight changes in the direction/orientation of Bp. Alternatively, as indicated earlier and as described below, the amplitude of Bp can be controlled by using coils and/or paramagnetic cores driven by coils. The effects would be the same as when physically moving permanent magnets.

This movement will serve a number of purposes: First, it will enhance detection sensitivity by the use of lock-in techniques. Secondly, since the external magnetic field is non-homogeneous, movement of the magnets translates to a change in the NMR resonance frequency (for a given spin) at a given distance from the probe tip. By controlling the resonance frequency and, separately, the form, duration, and rate of repetition of the RF pulses, additional information is obtainable regarding the NMR response of the tissue at a given distance from the probe tip. This will provide better characterization of the tissue's NMR response.

The movement of the magnets can also be used to provide information regarding the depth at which a change in the type of tissue occurs. The magnets are moved so that the field Bp strength at a given distance from the probe tip will be set to a chosen value. The RF pulses will be generated so as to enhance the NMR response from distances greater than the chosen distance from the probe tip. The differences in response of different types of tissue, at that chosen distance from the probe tip, can thus be used to locate the change in the type of tissue.

A Number of Possible Variations

FIGS. 8-14 illustrate a number of possible variations that may be made in the above-described apparatus.

Figure 8A:
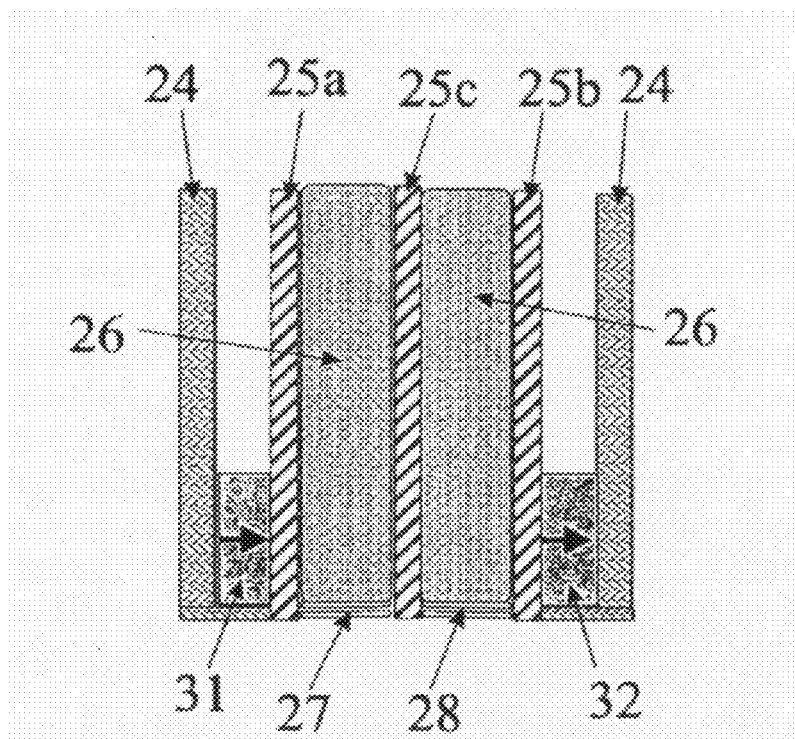
FIGS. 8a-8m illustrate a number of possible variations in the polarizing magnetic field and the transmission line ending in the apparatus of FIGS. 2-6.

FIG. 8*a* illustrates a variation wherein the inner conductive strip 25*c*, defining the inner conducting trace is extended up to the distal end of the probe head, making it flush with the outer conductive strips 25*a*, 25*b* defining the ground plates. The ends of the magnets 31, 32 could be flush with, or protruding, relative to the inner conducting trace 25*c* and ground plates 25*a*, 25*b*. The RF coils 27, 28 are then also moved to the probe distal end. The substance volume sampled is situated directly in contact with the probe end.

Figure 8B:
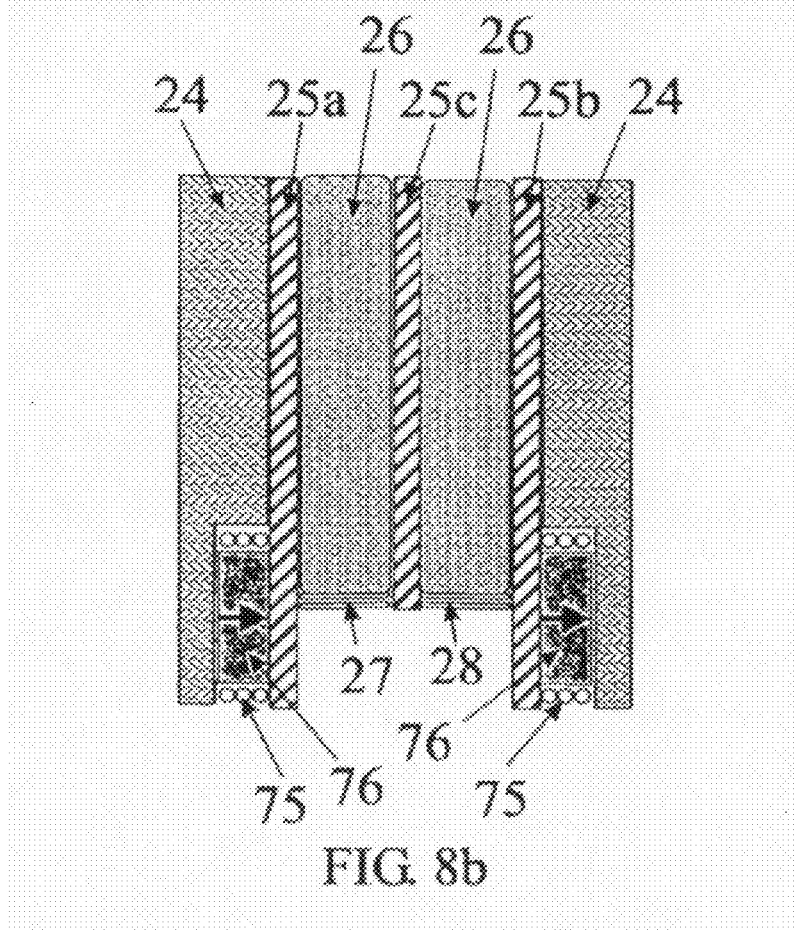

FIG. 8*b* illustrates a variation wherein the magnets are replaced by coils 75 surrounding paramagnetic cores 76, generating the polarizing field when current is driven through the coils. In this variation, the change in the amplitude of the polarizing field is performed by changing the intensity of the current through the coils. This current change induces a change in the magnetic field of the paramagnetic cores.

In another variation (not illustrated), the magnets could be replaced by coils, which will generate the polarizing field when current is driven through them. In this variation, the change in the amplitude of the polarizing field is performed by changing the intensity of the current transferred through the coils.

Figure 8C:
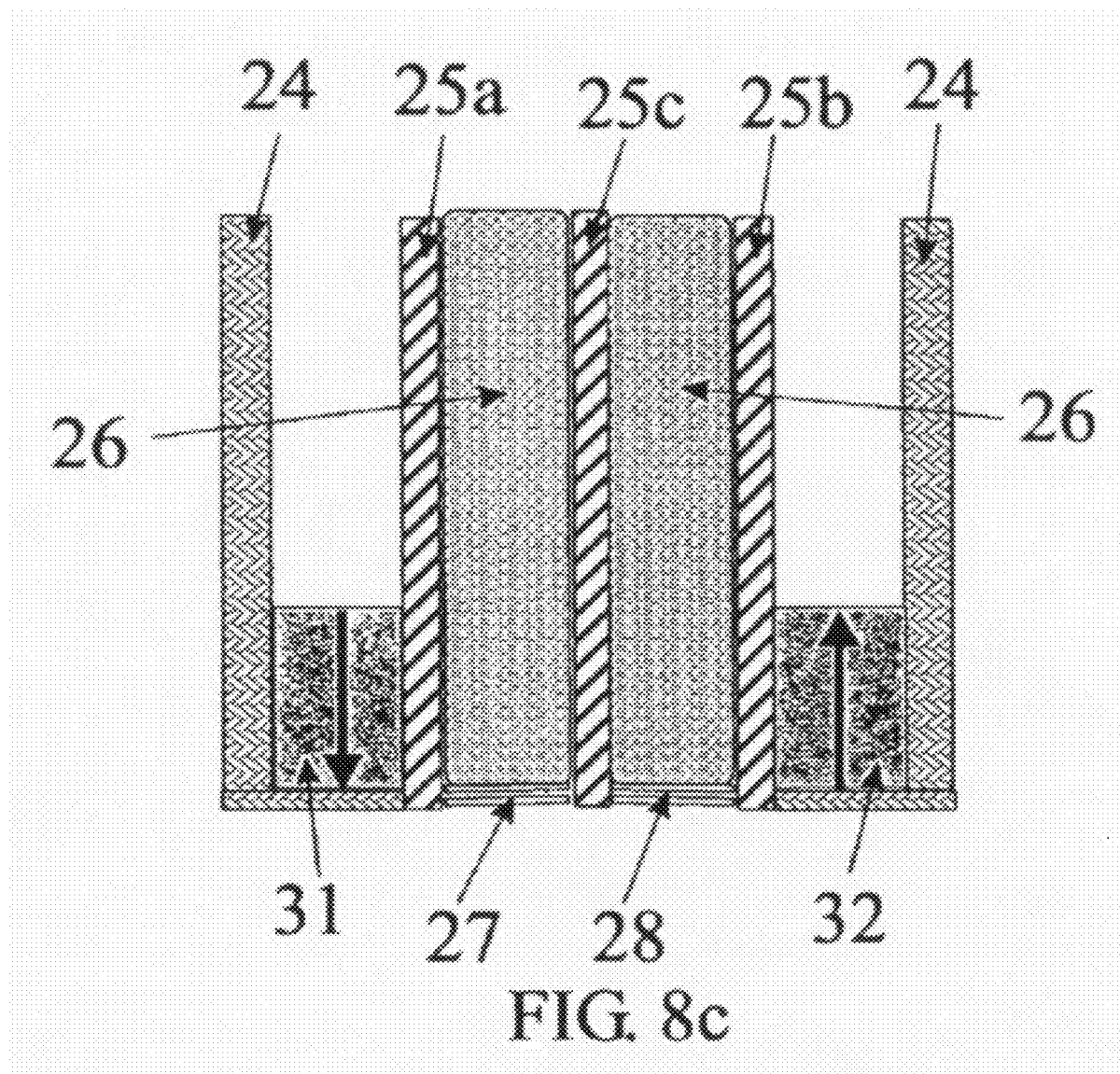

FIG. 8*c* illustrates a variation wherein the poles of the magnets 31, 32 are oriented in a direction parallel to the main axis of the probe head (the Y-direction, as defined for the preferred embodiment).

Figure 8D:
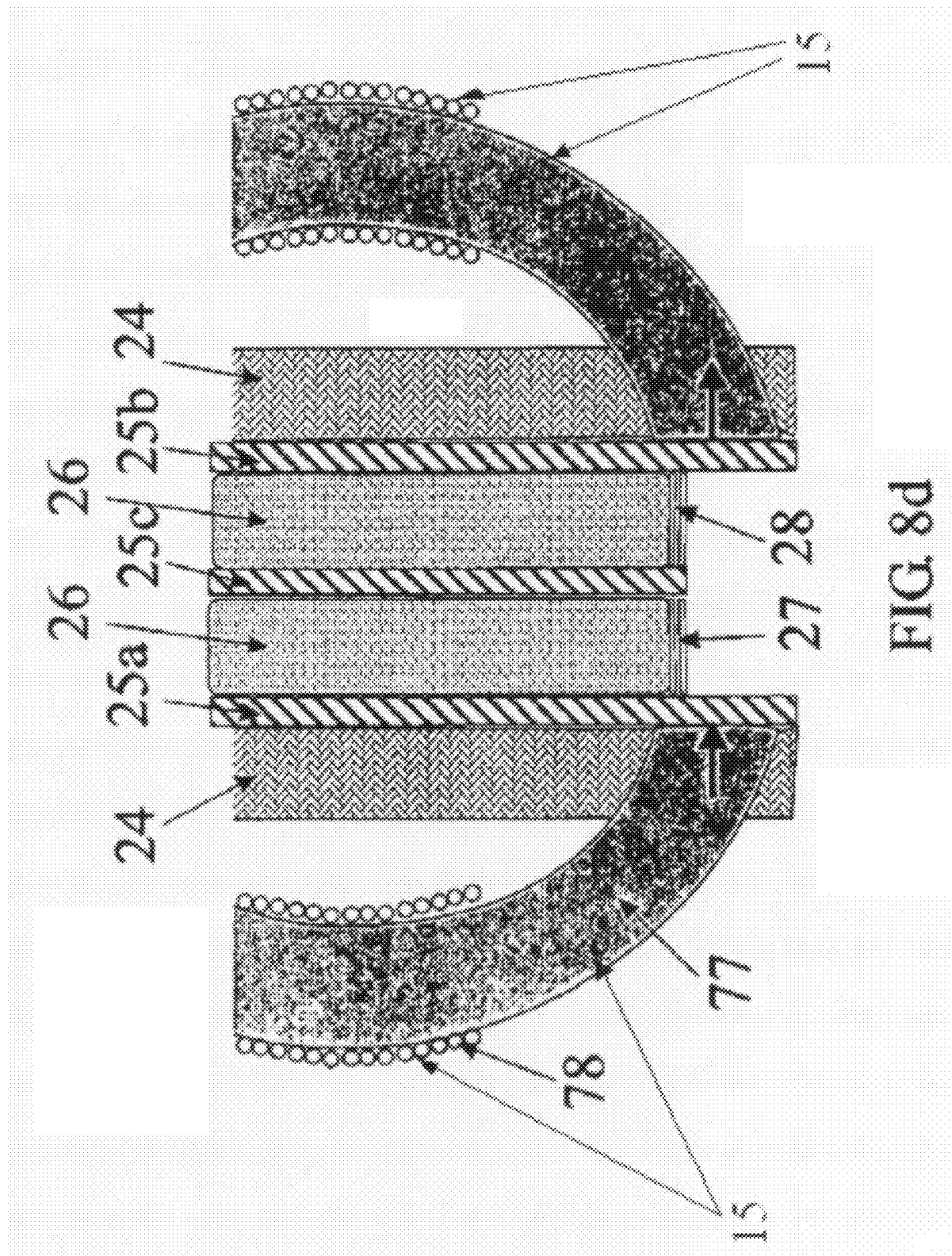

FIG. 8*d* illustrates a variation wherein the magnetic-field applicator 15 generating the polarizing magnetic field is formed as a "horse-shoe" shaped paramagnetic core 77, driven by a surrounding coil 78.

Figure 8E:
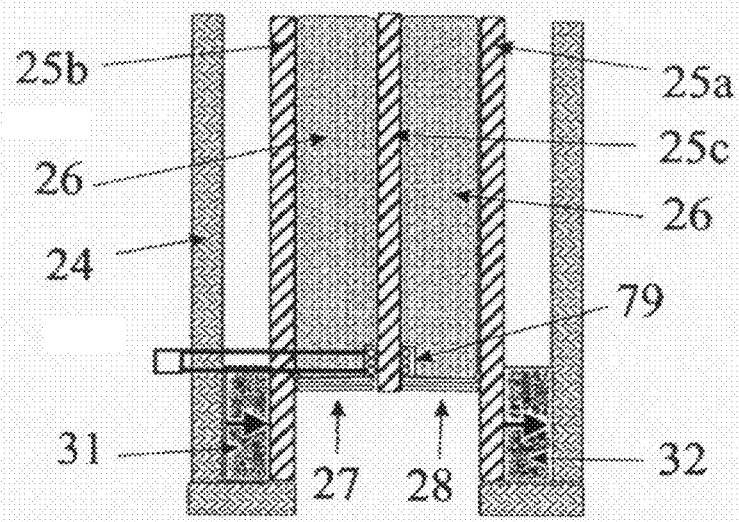

FIG. 8*e* illustrates a further variation wherein a current sensor, in the form, for example, of a pick-up coil 79, is placed near the distal end of the probe head to measure the current that passes through the examined substance. With this configuration a direct measurement of impedance can be made.

Figures 8F, 8G:
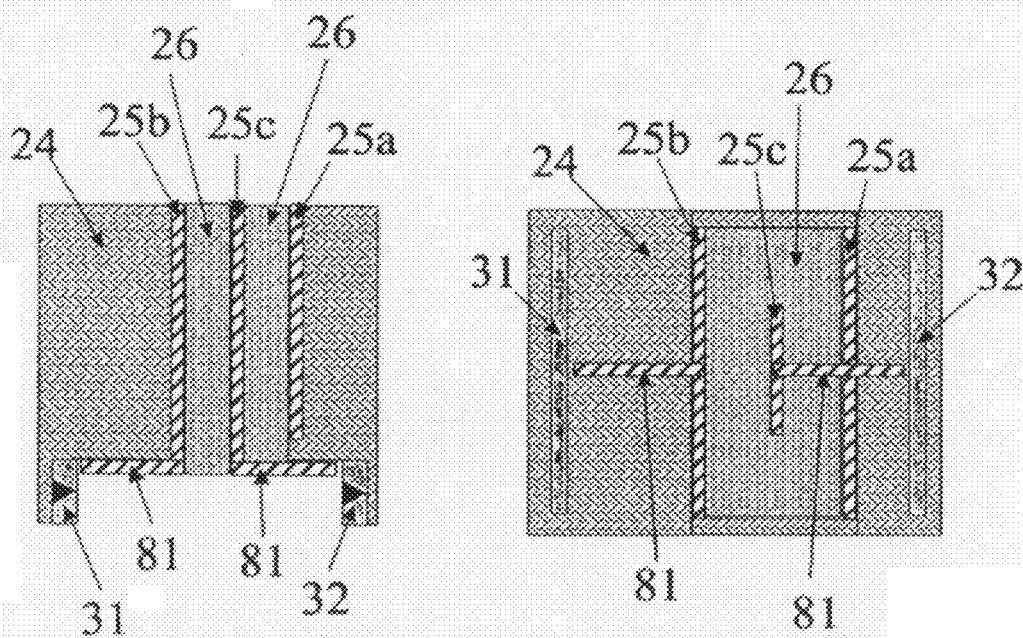
Figure 8H:
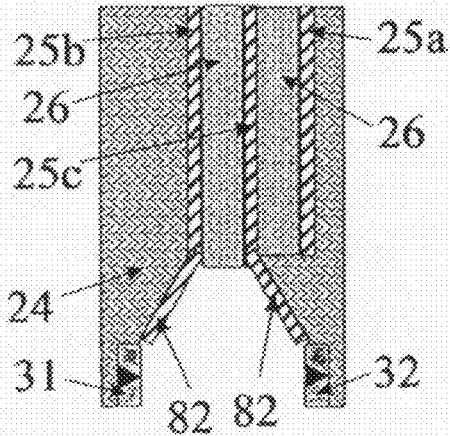
Figure 8I:
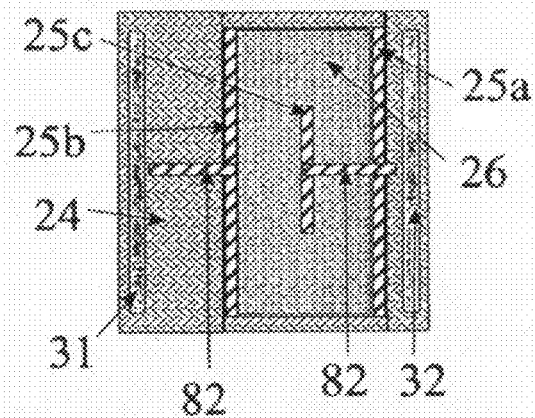
Figure 8J:
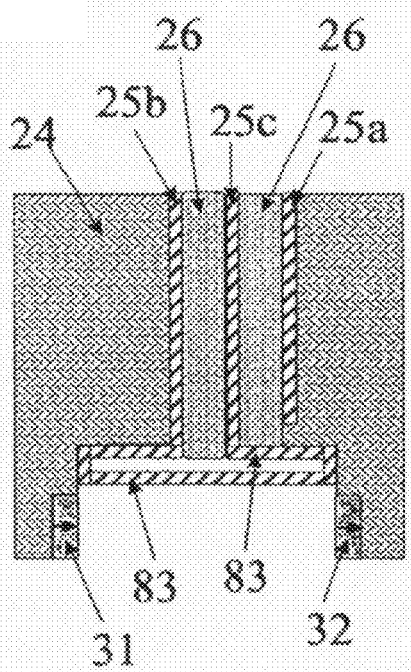
Figure 8K:
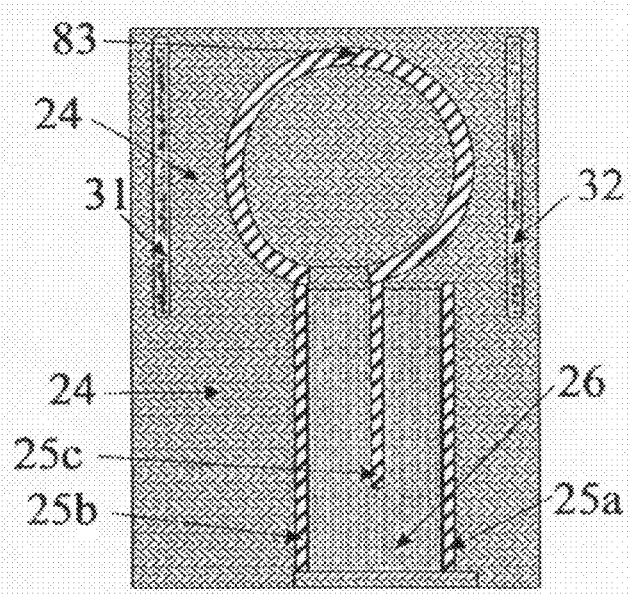

FIGS. 8*f*-8*k* are side and plan views illustrating further variations in the transmission line end structure: FIGS. 8*f*, 8*g* illustrate one ended by a dipole antenna 81. FIGS. 8*h*, 8*i* illustrate one ended by a V-shaped antenna 82; and FIGS. 8*j*, 8*k* illustrate one ended by a surface coil 83.

Figure 8L:
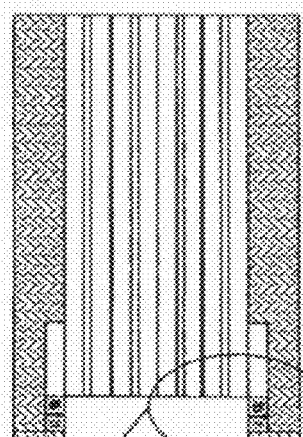
Figure 8M:
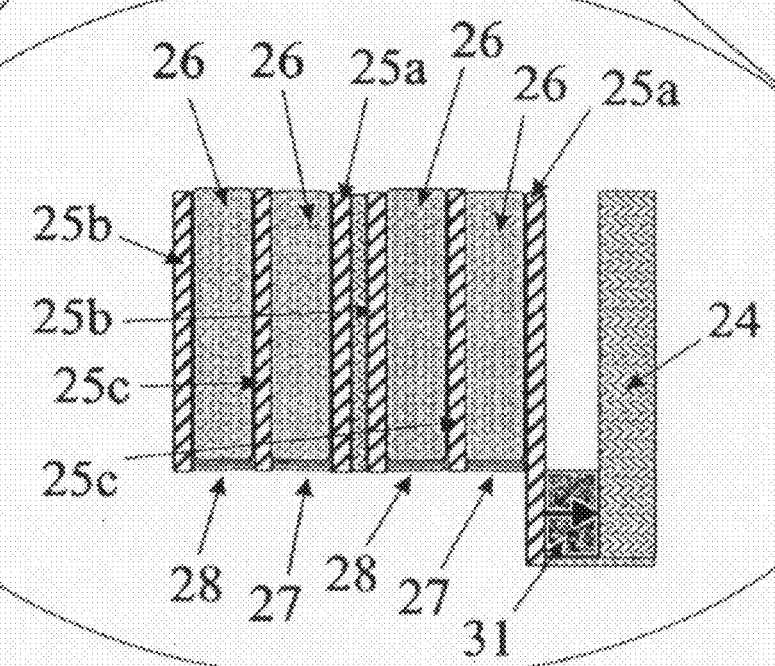

FIGS. 8*l*, 8*m* are side and enlarged views, respectively, illustrating yet another embodiment including an array of miniature sensors all sharing the same source of polarizing magnetic field 31, but each using different sources of RF radiation.

Figure 9A:
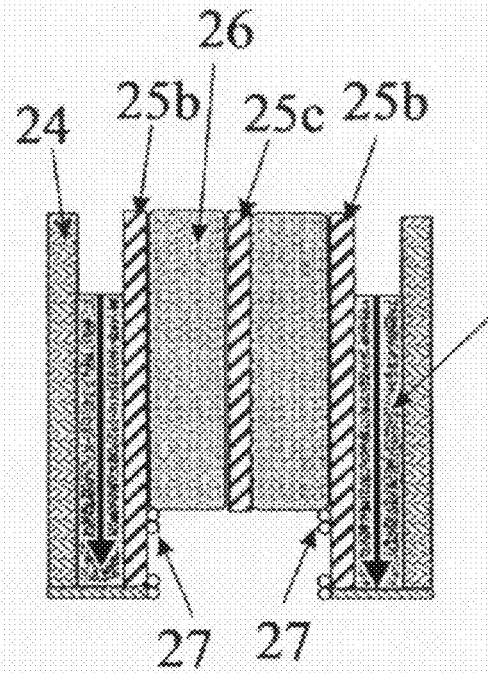
FIGS. 9a-9f illustrate further possible variations in the configurations of the polarizing magnetic field and transmission line.
Figure 9B:
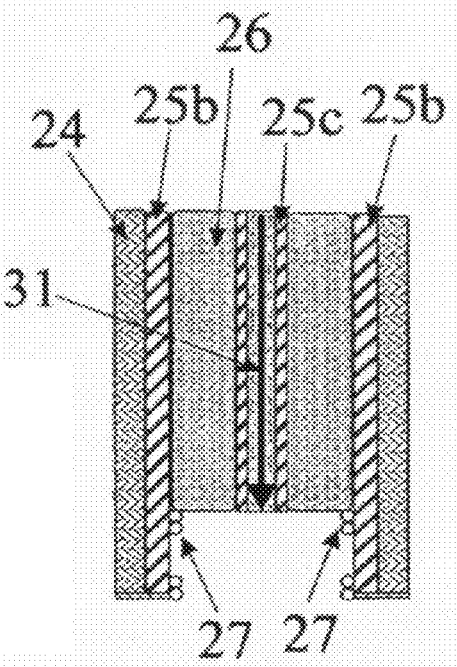
Figure 9C:
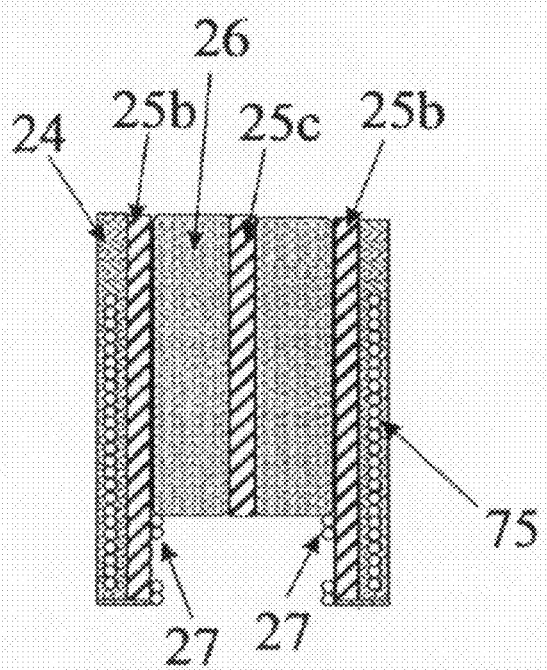
Figure 9D:
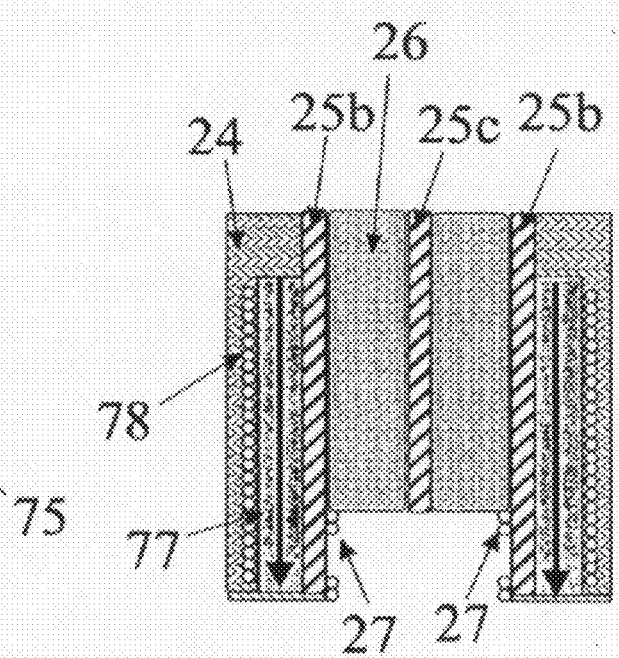

FIGS. 9*a*-9*d* illustrate further embodiments of the invention wherein the transmission line TL is of the cylindrical co-axial line type, having an inner conducting core 25*c*, surrounded by an insulator 26, which in turn is surrounded by a conductive cladding 25*b*. The polarizing magnetic field is generated by a movable concentric magnet 31, either surrounding the transmission line TL (FIG. 9*a*), or surrounded by the transmission line TL (FIG. 9*b*). In another variation, the magnet is replaced by coils 75 (FIG. 9*c*), or by coils 78 surrounding a paramagnetic core 77 (FIG. 9*d*). In the co-axial geometry, there is only one additional RF receiving coil needed. This coil is indicated in FIGS. 9*a*-9*d* by 27.

Figure 9E:
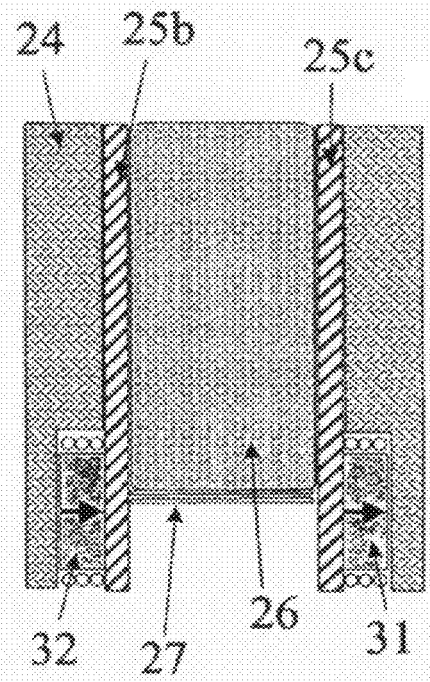
Figure 9F:
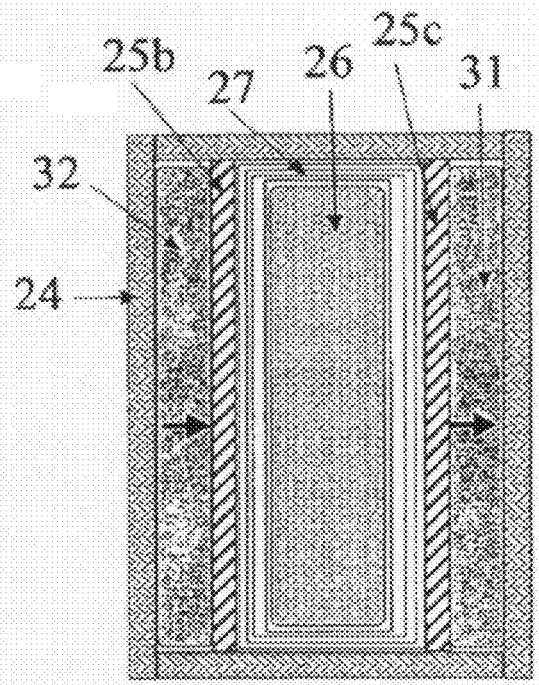

FIG. 9*e* (end view) and FIG. 9*f* (plan view) illustrate a further variation wherein the transmission line section is made of two conducting strips only, without an inner trace. One strip 25*b* serves as the ground plane, and the other strip 25*c* serves as the signal plane. With this configuration, only one RF coil 27 is needed in order to additionally collect NMR signals from the tissue.

Figure 10:
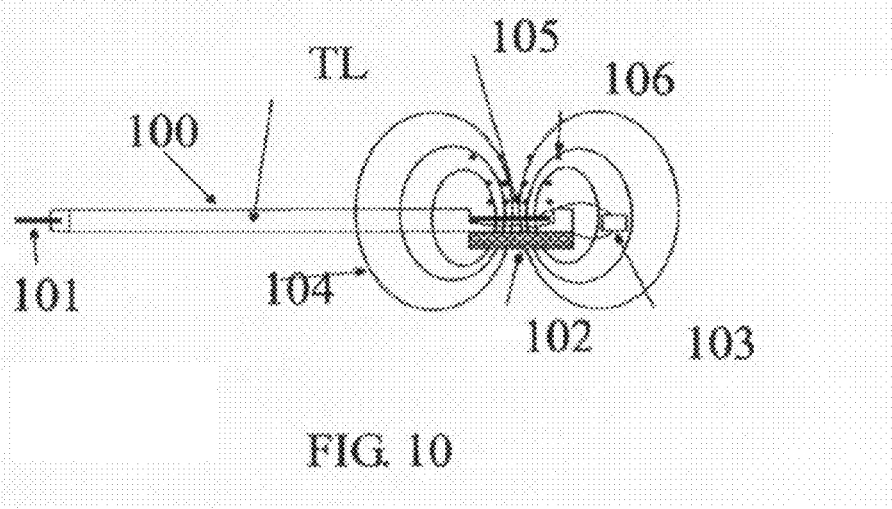
FIG. 10 diagrammatically illustrates a leaky transmission line configuration of sensing head in accordance with the present invention.

FIG. 10 illustrates another embodiment wherein the transmission line TL is open-sided and leaky. Thus, a section of the outer conductor 100 of the transmission line TL is cut off and forms a window 105. The inner conductor 401 continues up to the end of the transmission line TL. The inner conductor is electrically connected to an impedance tuning circuit 103. A permanent magnet 102 is placed below the transmission line. In this configuration, the polarizing field lines 104 of the permanent magnet have a component in the window zone perpendicular to the B-RF field 106 which in FIG. 10 extends outwardly from the page plane. The measurement is performed by advancing the probe so that the sampled tissue is positioned in the window 105.

Figure 11:
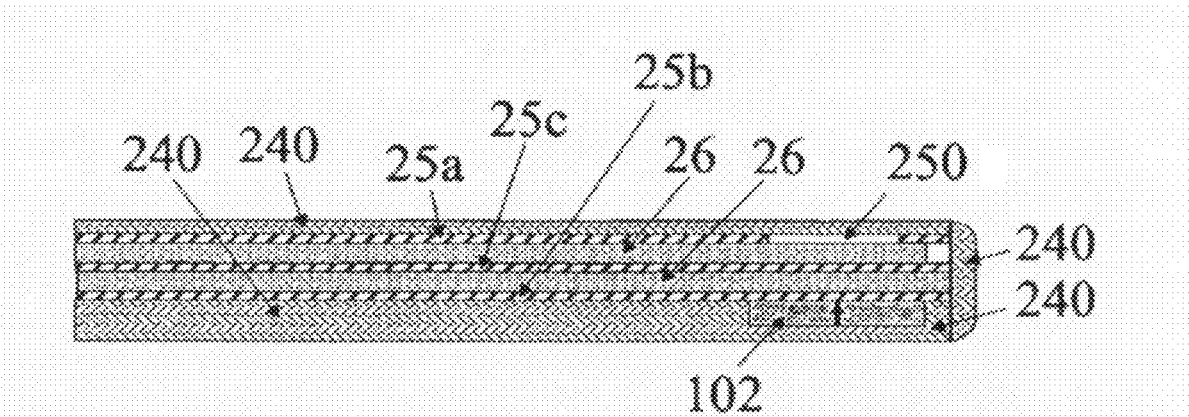
FIG. 11 illustrates the invention embodied in a catheter for insertion into the lumen of the patient's body.

FIG. 11 illustrates yet another embodiment wherein the sensing head of the probe is placed on the distal end of a catheter and inserted into a lumen of the body for inspection of the lumen walls. As also in the case of FIG. 10, the cut-off section of the outer conductor 250 allows for analysis of tissue near the region 250. The probe is covered by the catheter cladding 240.

Figure 12:
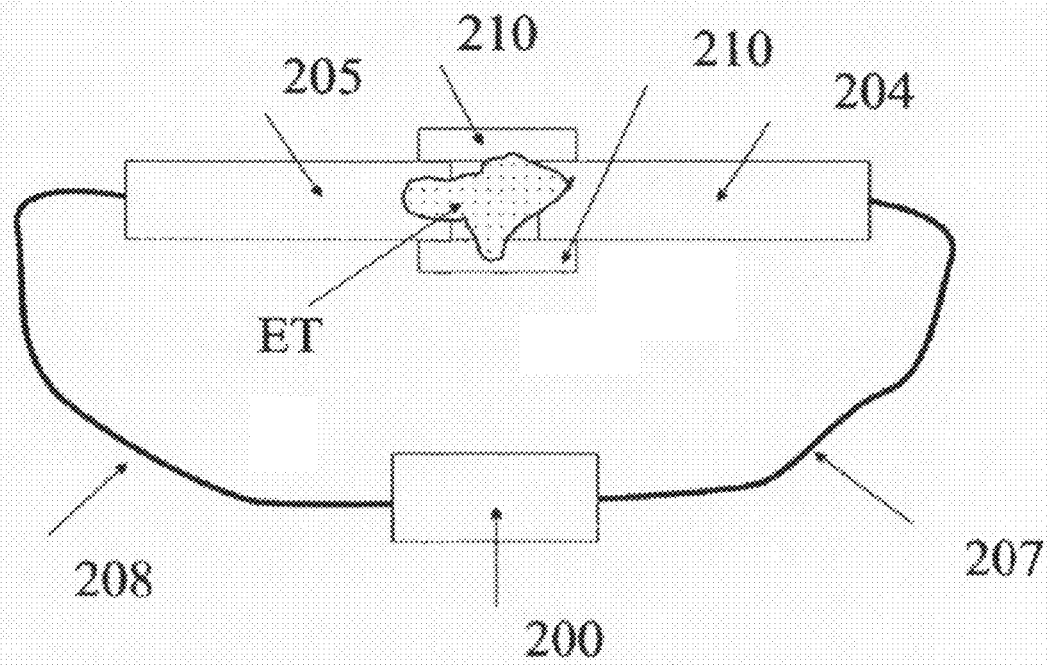
FIG. 12 illustrates apparatus constructed in accordance with the present invention including two sensing heads to be applied to opposite sides of the tissue being examined, as described in FIG. 2c.

FIG. 12 further illustrates the embodiment of FIG. 2c, wherein two probes, that is, sensing heads, are used in a transmitter/receiver configuration. In this configuration, one probe 204 acts in its turn as the transmitter, transmitting signals through the examined tissue ET, and the other probe 205 receives those signals and then in its turn act as a transmitter, while the first one acts as a receiver. In this mode of operation, both the reflected and transmitted signals are detected. The transmitted signals are fed through one transmission line 207, and the detected signals are transferred through another transmission line 208. Both transmission lines connect to the main unit 200. Magnets 210 are positioned so that they will generate the necessary polarizing field.

Figure 13:
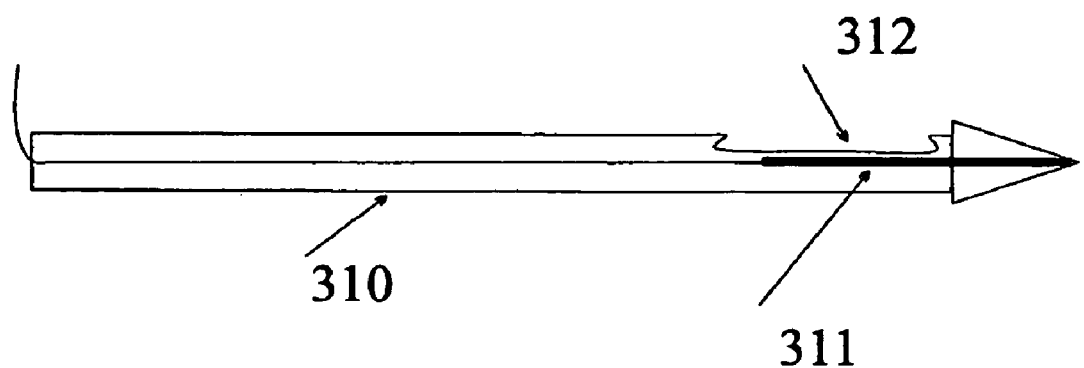
FIG. 13 diagrammatically illustrates a sensing head in accordance with the present invention incorporated in a biopsy needle.

FIG. 13 illustrates another embodiment wherein the sensing head of the probe 311 is placed inside a biopsy core needle 310. The probe continuously inspects the tissue type at the tip of the needle, as the needle is passing, from the outer skin surface to the biopsy site. Suspected tissue will be excised, for example, using a tissue-collecting cavity 312.

Figure 14:
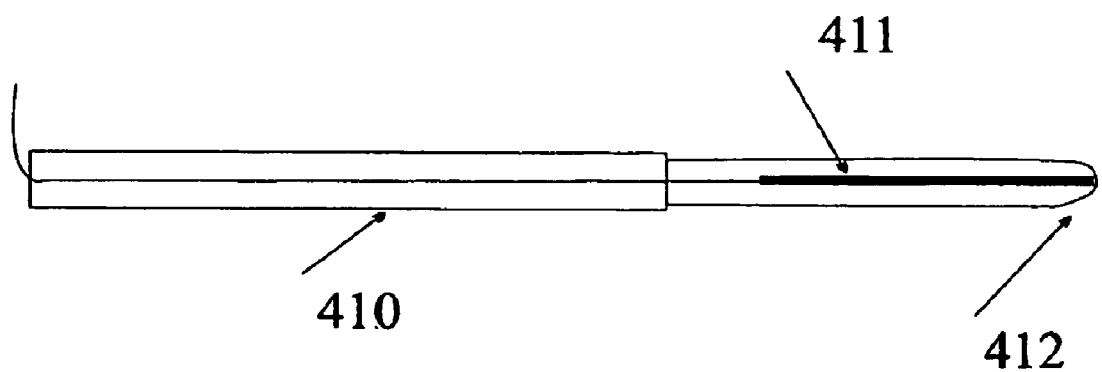
FIG. 14 illustrates a sensing head constructed in accordance with the present invention incorporated in a cutting tool so as to enable obtaining an indication of the tissue type in real time during a surgical operation.

FIG. 14 illustrates yet another embodiment wherein the sensing head of the probe 411 is conjugated to a cutting tool, comprised of a handle 410 and a cutting head 412, so that tissue recognition may be made prior to each excision cut.

In the above described embodiments, contrasting agents (for example: gadodiamide or mangafodipir) for the enhancement of the NMR signal for the characterization of various tissue parameters may also be applied to the examined tissue, either locally, or intravenously.

The RF sequence fed into the sensor through the transmission line may consist of combinations of repetitive pulses, some optimized for the EI measurement and some optimized for EPR (electron paramagnetic resonance) measurements. The polarizing magnetic field may also be optimized for the detection of EPR signals. Contrasting agents (for example: activated charcoal, or cabamoyl-proxyl, or trityl-methyl based OX 031, OX036) to enhance the EPR signal for better characterization of various tissue parameters, may also be applied to the examined tissue, either locally or intravenously.

The RF sequence fed into the sensor through the transmission line may also consist of combinations of repetitive pulses in which some are optimized for the EI measurement, and some are optimized for Proton Electron Double Resonance (PEDR), also known as Overhauser MR, measurements. The polarizing magnetic field is also optimized for the detection of PEDR signals. Contrasting agents to enhance the Overhauser signal for the better characterization of various tissue parameters, may also be applied to the examined tissue, either locally, or intravenously.

It will be appreciated that the tissue may be a biopsy sample of a living tissue. Additionally, characterization of the tissue type may relate to identifying a malignancy or another pathology.

It will also be appreciated that the invention could also be used for identifying other types of substances, for example, in situ characterization of composition of bore-hole walls, and in situ characterization of polymer and elastomer products and coatings.

Many other implementations of the invention, including additional variations and applications thereof, will be apparent to those skilled in the art.

REFERENCES

1. Surowiex, A. J. et al., 1988, Dielectric Properties of Breast Carcinoma and the Surrounding Tissues, IEEE Trans. Biomed. Eng. 35(4):257-262.
2. Heintz, J.& O. Minet, 1995 Dielectric Properties of Female Breast Tumors, In Ninth International Conference on Electrical Bio-Impedance, Heidelberg.
3. Liefn, D. et al., 1998 Clinical Study on Electrical Impedance Method Used Diagnosis of Breast Diasi. In Tenth International Conference on Electrical Bio-Impedance. Barcelona.
4. Morimoto, et al., Measurement of Electrical Bio-Impedance of Breast Tumors, Eu. Serg. Res. 2292:86-92, 1990.
5. Dexter, G. et al, "In-Vivo Measurement of Tumor Conductiveness With Magnetic Bioimpedance Method", IEEE Trans Biomedical Engine", Vol. 47 No. 10 October 2000.
6. Prthig, R., (1978), Dielectric and Electronic Properties of Biological Materials, John Wiley, New York.
7. Schanna, O. F. et al., (1978), Impedance Measurement in Biological Cell. John Wiley, New York.
8. H. P. Schwan, Mechanisms Responsible for Electrical Properties of Tissue and Cell Suspensions, Med. Prog. Tech. 19:163-165, 1993.
9. Fricke, H. The Theory of Electrolytic Polarization. Philosophical Magazine 1932; (97):310-318.
10. Cole K S (19721 Membranes, Ions (1978) and Impulses. University of California Press, Berkeley.

What is claimed is:

1. Apparatus for examining a substance of a given volume, to characterize the examined substance type, the apparatus comprising:

a magnetic-field applicator, for applying locally a polarizing magnetic field through the substance of the given volume, with a component defining a polarizing axis;

a first sensing head, adapted for placement proximally to the substance of the given volume, the first sensoring head comprising a first main component, configured for:

applying locally Radio Frequency (RF) pulses to the substance of the given volume, the RF pulses having a B component, orthogonal to the polarizing axis, such as to invoke Electrical Impedance (EI) response signals corresponding to the EI of the examined substance of the given volume, and Magnetic Resonance (MR) response signals corresponding to the MR properties of the examined substance of the given volume;

detecting locally said EI response signals from the substance of the given volume; and detecting locally said MR response signals from the substance of the given volume; and a second sending head, wherein the first sensing head is configured for interacting with at least said second sensing head.

2. The apparatus of claim 1, wherein the first main component comprises an auxiliary detector configured for directional detecting locally of:
MR response signals whose direction has a component in the direction of the B component of the RF pulses.

3. The apparatus of claim 2, wherein said auxiliary detector is further configured for detecting locally said MR response signals whose direction has a component orthogonal to the B component of the RF pulses and orthogonal to the polarizing axis.

4. The apparatus of claim 3, wherein the auxiliary detector includes at least one coil at a proximal end of said first sensing head, with respect to the substance of the given volume, the coil being configured to detect the MR signals whose direction has a component orthogonal to the B component of the RF pulses and orthogonal to the polarizing axis.

5. The apparatus of claim 2, wherein the first main component further includes:
an inner conductive strip extending parallel to a longitudinal axis of the first sensing head:
a pair of outer conductive strips, electrically connected to each other, extending parallel to, and on opposite sides of, the inner conductive strip, and separated therefrom by insulation; and
said auxiliary detector further comprises
a first RF coil located between the inner conductive strip and one of the outer conductive strips and extending perpendicularly to the longitudinal axis; and
a second RF coil located between the inner conductive strip and the other of the outer conductive strips and extending perpendicularly to the longitudinal axis.

6. The apparatus of claim 2, wherein the first main component further comprises:
a first conductive strip extending parallel to the longitudinal axis;
a second conductive strip extending parallel to the first conductive strip and separated therefrom by insulation;
said auxiliary detector further comprises an RF coil located between the first and second conductive strips and extending perpendicularly to the longitudinal axis of a transmission line.

7. The apparatus of claim 1, wherein a proximal end of the first sensing head, with respect to the substance of the given volume, has a structure, selected from the group consisting of an open end, a dipole, a V-shaped antenna, a conical antenna, a surface coil, a single-sided leaky end, and an open cavity.

8. The apparatus of claim 1, and further including:
an electrical control and processing system; and
a first transmission line for providing communication between the first sensing head and the electrical control and processing system.

9. The apparatus of claim 8, wherein the electrical control and processing system utilizes the EI and MR response signals in characterizing the examined substance type, based on electrical impedance and the magnetic resonance properties of the examined substance of the given volume.

10. The apparatus of claim 8, wherein the electrical control and processing system is configured to vary the polarizing magnetic field such as to vary the RF and the MR response signals.

11. The apparatus of claim 8 wherein a proximal end of the first sensing head, with respect to the substance of the given volume, is electrically connected to a tuning circuit, permitting the impedance of the first sensing head to be varied and thereby to vary the reflectivity of the applied RF pulses.

12. The apparatus of claim 8, wherein the second sensing head is constructed substantially as the first sensing head, and further including a second transmission line, for providing communication between the second sensing head and the electrical control and processing system.

13. The apparatus of claim 12, wherein:
the first sensing head is adapted for placement proximally to a first location of the substance of the given volume; and
the second sensing head is adapted for placement proximally to a second location of the substance of the given volume,
wherein both the first and second sensing heads operate together, as follows:
each of the first and second sensing heads applying locally RF pulses to the substance of the given volume, the RF pulses having a B component, orthogonal to the polarizing axis;
each of the first and second sensing heads is configured for detecting locally EI response signals from the substance of the given volume; and
each of the first and second sensing heads is configured for detecting locally MR response signals from the substance of the given volume.

14. The apparatus of claim 13, wherein:
said first and second sensing heads are operable for detecting EI response signals which are selected from the group consisting of EI response signals reflected from the substance of the given volume, EI response signals transmitted through the substance of the given volume, and a combination thereof; and
MR response signals which are selected from the group consisting of MR response signals reflected from the substance of the given volume, MR response signals transmitted through the substance of the given volume, and a combination thereof.

15. The apparatus of claim 12, wherein:
the first sensing head is placeable proximally to a first location of the substance of the given volume; and
the second sensing head is placeable proximally to a second location of the substance of the given volume.

16. The apparatus of claim 15, wherein one of either the first or second sensing heads is configured for detecting:
the EI response signals, which are selected from the group consisting of EI response signals reflected from the substance of the given volume, EI response signals transmitted through the substance of the given volume, and a combination thereof; and
the MR response signals, which are selected from the group consisting of MR response signals reflected from the substance of the given volume, MR response signals transmitted through the substance of the given volume, and a combination thereof.

17. The apparatus of claim 15, wherein the first sensing head and the second sensing head are further placeable to form an arc of at least 90 degrees vis a vis a centerline of the substance of the given volume.

18. The apparatus of claim 15, wherein the first sensing head and the second sensing head are further placeable to form an arc of at least 130 degrees vis a vis a centerline of the substance of the given volume.

19. The apparatus of claim 15, wherein the electrical control and processing system is further configured for alternating a task of being a transmitter between the first and second sensing heads.

20. The apparatus of claim 8, and further including:
additional of sensing heads, each constructed substantially as the first sensing head; and
a plurality of transmission lines, each dedicated to one of additional sensing heads, for providing communication between each of additional sensing heads and the electrical control and processing system.

21. The apparatus of claim 20, wherein:
each of said additional sensing heads are further configured for detecting EI response signals which are selected from the group consisting of EI response signals reflected from the substance of the given volume, EI response signals transmitted through the substance of the given volume, and a combination thereof; and
MR response signals which are selected from the group consisting of MR response signals reflected from the substance of the given volume, MR response signals transmitted through the substance of the given volume, and a combination thereof.

22. The apparatus of claim 8, wherein the electrical control and processing system is configured to process the detected EI response signals invoked by the RF pulses, calculate an effective electrical impedance of the examined substance of the given volume, and utilizes the calculated electrical impedance in characterizing the examined substance type.

23. The apparatus of claim 8, wherein the electrical control and processing system is configured to apply RF pulses, capable of invoking MR free induction decay (FID) signals, corresponding to echoes from excited spins in the examined substance of the given volume when returning to equilibrium, detect the FID signals, and utilize the detected FID signals in characterizing the examined substance type.

24. The apparatus of claim 8, configured for varying the polarizing magnetic field such as to vary the EI response signals and the MR response signals.

25. The apparatus of claim 8, wherein said electrical control and processing system is configured for applying said RF pulses as a sequence of pulses; said sequence of pulses comprising pulses optimized for EI measurements, and pulses optimized for MR measurements.

26. The apparatus of claim 8, wherein said electrical control and processing system is configured for analyzing the detected MR response signals for at least one parameter, selected from the group consisting of: spin density, longitudinal relaxation time (T1), transverse relaxation time (T2) of the examined substance volume, and a combination thereof.

27. The apparatus of claim 8, wherein said electrical control and processing system is configured for detecting and processing said EI and MR response signals by:
collecting the EI response signals and the MR response signals;
analyzing said collected response signals for predetermined type parameters characterizing the examined substance volume type;
modeling the type parameters into a set of type parameters; and
classifying said set of type parameters according to known parameter sets indicative of known type substance types.

28. The apparatus of claim 1, wherein a strength of the magnetic field generated by the RF pulses is varied.

29. The apparatus of claim 1, wherein the magnetic-field applicator is selected from the group consisting of two permanent magnets and a "horse-shoe" shaped paramagnetic core, driven by a surrounding coil.

30. The apparatus of claim 1, wherein the magnetic-field applicator is integrated with the first sensing head.

31. A method for examining a substance of a given volume, to characterize the examined substance type, the method comprising:
applying locally a polarizing magnetic field through the substance of the given volume, with a component defining a polarizing axis;
applying locally Radio Frequency (RF) pulses to the substance of the given volume, the RF pulses having a B component, orthogonal to the polarizing axis, such as to invoke Electrical Impedance (EI) response signals corresponding to the EI) of the examined substance of the given volume, and magnetic resonance (MR) response signals corresponding to the MR properties of the examined substance of the given volume;
detecting locally, by first and second sensing heads, EI response signals from the substance of the given volume; and
detecting locally, by said first and second sensing heads, MR response signals from the substance of the given volume.

32. The method of claim 31, wherein said detecting locally MR response further includes detecting locally MR response signals whose direction has a component in the direction of the B component of the RF pulses.

33. The method of claim 31, wherein said detecting locally MR response further includes detecting locally MR response signals whose direction has a component orthogonal to the B component of the RF pulses and orthogonal to the polarizing axis.

34. The method of claim 31, and further including utilizing the EI and MR response signals in characterizing the examined substance type, based on electrical impedance and the magnetic resonance properties of the examined substance of the given volume.

35. The method of claim 31, and further including varying the polarizing magnetic field such as to vary the EI response signals and the MR response signals.

36. The method of claim 31, and further including varying a reflectivity of the applied RF pulses.

37. The method of claim 31, and further including tuning a strength of the magnetic field generated by the RF pulses.

38. The method of claim 31, and further including:
applying locally, from first and second locations, proximal to the substance of the given volume, RF pulses to the substance of the given volume, the RF pulses having a B component, orthogonal to the polarizing axis;
detecting locally from the first and second locations EI response signals from the substance of the given volume; and
detecting locally from the first and second locations MR response signals from the substance of the given volume.

39. The method of claim 38, wherein:
the EI response signals are selected from the group consisting of EI response signals reflected from the substance of the given volume, EI response signals transmitted through the substance of the given volume, and a combination thereof; and
the MR response signals are selected from the group consisting of MR response signals reflected from the substance of the given volume, MR response signals transmitted through the substance of the given volume, and a combination thereof.

40. The method of claim 31, wherein:
applying locally, from a first location, proximal to the substance of the given volume, RF pulses to the substance of the given volume, the RF pulses having a B component, orthogonal to the polarizing axis;

detecting locally, from the first location and a second location, proximal to the substance of the given volume, EI response signals from the substance of the given volume; and detecting locally, from the first location and the second location, MR response signals from the substance of the given volume.

41. The method of claim 40, wherein:
at the first location:
the EI response signals are reflected EI response signals; and
the MR response signals are reflected MR response signals; and
at the second location:
the EI response signals are selected from the group consisting of EI response signals reflected from the substance of the given volume, EI response signals transmitted through the substance of the given volume, and a combination thereof; and
the MR response signals are selected from the group consisting of MR response signals reflected from the substance of the given volume, MR response signals transmitted through the substance of the given volume, and a combination thereof.

42. The method of claim 10, wherein said detecting said EI response signals and said detecting said MR response signals is preceded by locating the first sensing head and the second sensing head locations form an arc of at least 90 degrees vis a vis a centerline of the substance of the given volume.

43. The method of claim 40, wherein said detecting said EI response signals and said detecting said MR response signals is preceded by locating the first sensing head and the second sensing head to form an arc of at least 130 degrees vis a vis a centerline of the substance of the given volume.

44. The method of claim 40, and further including alternating the applying locally between the first and second locations.

45. The method of claim 31, and further including:
applying locally, from a plurality of locations proximal to the substance of the given volume, RF pulses to the substance of the given volume, the RF pulses having a B component, orthogonal to the polarizing axis;
detecting locally from the plurality of the locations EI response signals from the substance of the given volume; and
detecting locally from the plurality of the locations MR response signals from the substance of the given volume.

46. The method of claim 45, wherein:
the EI response signals are selected from the group consisting of EI response signals reflected from the substance of the given volume, EI response signals transmitted through the substance of the given volume, and a combination thereof; and
the MR response signals are selected from the group consisting of MR response signals reflected from the substance of the given volume, MR response signals transmitted through the substance of the given volume, and a combination thereof.

47. The method of claim 31, and further including:
applying locally, from a first location proximal to the substance of the given volume, RF pulses to the substance of the given volume, the RF pulses having a B component, orthogonal to the polarizing axis;
detecting locally from the first location and a plurality of additional locations, proximal to the substance of the given volume, EI response signals from the substance of the given volume; and detecting locally from the first location and the plurality of the locations MR response signals from the substance of the given volume.

48. The method of claim 47, wherein:
at the first location:
the EI response signals are reflected EI response signals; and
the MR response signals are reflected MR response signals; and
at the plurality of additional locations:
the EI response signals are selected from the group consisting of EI response signals reflected from the substance of the given volume, EI response signals transmitted through the substance of the given volume, and a combination thereof; and
the MR response signals are selected from the group consisting of MR response signals reflected from the substance of the given volume, MR response signals transmitted through the substance of the given volume, and a combination thereof.

49. The method of claim 48, and further including rotating the first location among the plurality of locations, at different times.

50. The method of claim 31, wherein the invoked and detected MR response signals are selected from the group consisting of NMR signals, EMR signals, and a combination thereof.

51. The method of claim 31, wherein said examining said substance is further performed on a tissue, in vivo.

52. The method of claim 31, wherein said examining said substance is further performed on a human tissue, in vivo.

53. The method of claim 31, wherein said examining said substance comprises a biopsy.

54. The method of claim 31, wherein said examining said substance is further performed on a tissue characterized for malignancy.

55. The method of claim 31, wherein said examining said substance is further performed on a tissue characterized for pathology.

56. The method of claim 31, wherein said examining said substance is further performed on organic matter.

57. The method of claim 31, wherein said examining said substance is further performed on inorganic matter.

58. The method of claim 31, and further including:
processing the detected EI response signals invoked by the RF pulses;
calculating an effective electrical impedance of the examined substance of the given volume; and
utilizing the calculated electrical impedance in characterizing the examined substance type.

59. The method of claim 31, wherein:
said applying further includes applying RF pulses capable of invoking MR free induction decay (FID) signals, corresponding to echoes from excited spins in the examined substance of the given volume when returning to equilibrium;
and wherein the method further includes:
detecting the FID signals; and
utilizing the detected FID signals in characterizing the examined substance type.

60. The method of claim 31, wherein said applying further includes applying said RF pulses as a sequence of pulses, said sequence of pulses comprising pulses optimized for EI measurements, and pulses optimized for MR measurements.

61. The method of claim 31, and further including analyzing the detected MR response signals of at least one parameter, selected from the group consisting of: spin density, longitudinal relaxation time (T1), transverse relaxation time (T2) of the examined substance volume, and a combination thereof.

62. The method of claim 31, and further including processing EI and MR response signals by:
- collecting the EI response signals and the MR response signals;
- analyzing said collected response signals for predetermined type parameters characterizing the examined substance volume type;
- modeling the type parameters into a set of type parameters; and
- classifying said set of type parameters according to known type parameter sets indicative of known substance types.

63. The method of claim 31, wherein the MR response signals are NMR response signals, which are enhanced by a prior injection of a contrast agent.

64. The method of claim 31, wherein the MR response signals are EMR response signals, which are enhanced by a prior injection of a contrast agent.

* * * * *